(12) United States Patent
Lynch et al.

(10) Patent No.: US 6,579,267 B2
(45) Date of Patent: Jun. 17, 2003

(54) PIVOTING JOINT INFUSION ASSEMBLY

(75) Inventors: George R. Lynch, Coppell, TX (US); Andrew Nelson, Dallas, TX (US); Gilles Petitjean, Issoudun (FR)

(73) Assignee: Applied Diabetes Research, Inc., Carrollton, TX (US)

( * ) Notice: Subject to any disclaimer, the term of this patent is extended or adjusted under 35 U.S.C. 154(b) by 0 days.

(21) Appl. No.: 09/896,149

(22) Filed: Jun. 29, 2001

(65) Prior Publication Data

US 2002/0095138 A1 Jul. 18, 2002

Related U.S. Application Data

(60) Provisional application No. 60/259,971, filed on Jan. 5, 2001.

(51) Int. Cl.[7] .......................... A61M 5/32; A61M 5/00; A61M 25/00; A61M 5/178
(52) U.S. Cl. ..................... 604/174; 604/178; 604/179; 604/180; 604/264; 604/161; 604/164.01; 604/164.04; 604/164.07; 604/165.01; 604/165.03; 604/93.01
(58) Field of Search .......................... 604/890.1, 93.01, 604/115, 158, 161, 164.01, 164.04, 164.07, 165.01, 165.03, 174, 178–180, 264; 128/DIG. 26, DIG. 6

(56) References Cited

U.S. PATENT DOCUMENTS

| | | | | |
|---|---|---|---|---|
| 4,755,173 A | * | 7/1988 | Konopka et al. | 604/167 |
| 5,176,662 A | * | 1/1993 | Bartholomew et al. | 604/283 |
| 5,545,143 A | * | 8/1996 | Fischell | 604/180 |
| 5,968,011 A | * | 10/1999 | Larsen et al. | 604/93 |
| 6,017,328 A | * | 1/2000 | Fischell et al. | 604/180 |
| 6,095,997 A | * | 8/2000 | French et al. | 604/9 |

* cited by examiner

*Primary Examiner*—David J. Walczak
*Assistant Examiner*—Anuradha Ramana
(74) *Attorney, Agent, or Firm*—Jackson Walker L.L.P.

(57) ABSTRACT

System for the subcutaneous delivery into the body of a patient of a fluid from a remote vessel. The system includes a main assembly and placement member with a needle. A delivery tube for carrying the fluid is attached at a near end to the remote reservoir or vessel. At removed end, the delivery tube has a needle for engagement with the main assembly. The main assembly includes a rotating member that when the rotating is perpendicular to the main assembly, it will accept the handle and needle for emplacement of the body onto a patient. After the handle and needle are removed, the delivery tube can be attached to the rotating member which can then be rotated down to a position along to and adjacent the skin of the patient. This provides for a flush mounted infusion device.

22 Claims, 56 Drawing Sheets

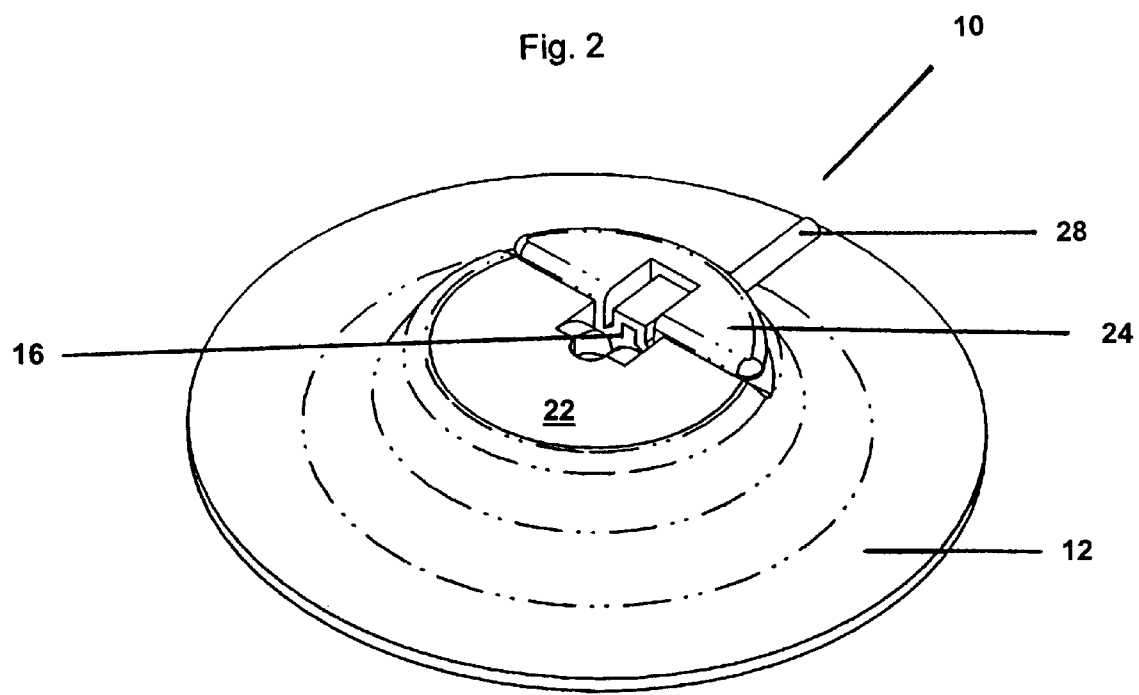

SECTION A-A

SECTION B-B

SECTION A-A

SECTION B-B

SECTION A-A

SECTION A-A

SECTION B-B

SECTION A-A

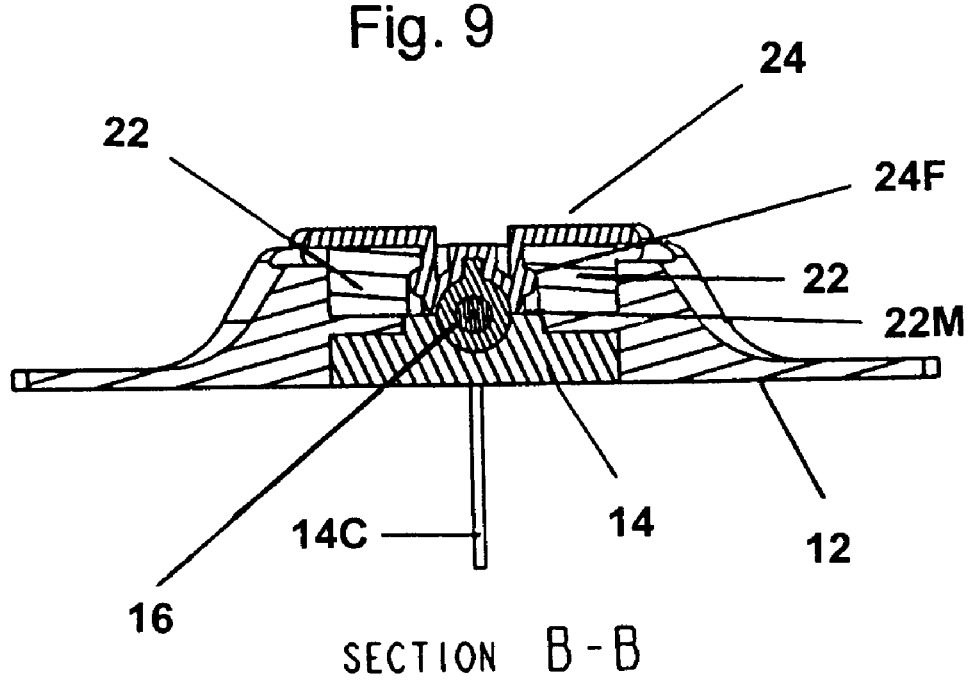

SECTION B-B

SECTION A-A

SECTION B-B

SECTION A-A

SECTION A-A

122"P

122"O
122"M
122"N

DETAIL C
SCALE 20/1

SECTION A-A

SECTION A-A

SECTION B-B

SECTION A-A

PIVOTING JOINT INFUSION ASSEMBLY

This application claims priority from U.S. Provisional Application No. 60/259,971 filed Jan. 5, 2001.

FIELD OF THE INVENTION

A device for subcutaneous delivery of a fluid to the patient, the device comprising a body having a rotating member, the rotating member in a first position for the emplacement of the device onto the body of patient and in a second position for delivery of a fluid into the patients body.

BACKGROUND

The purpose of a fluid injection system or infusion assembly is to transport fluids, such as insulin, from a container remote from a patient's body, through a tube to an assembly, including a cannula, that will allow the introduction of the fluid into the body of the patient. The fluid injection assembly is designed to be worn on the skin of a patient, such as on the abdomen of the patient for injecting fluids such as insulin, or other subcutaneously administered drugs into the body of the patient.

From time to time, however, it is often necessary for the patient to disconnect the tube between the remote fluid container and the fluid injection assembly so as to, for example, take a shower. It can be appreciated that a fluid injection system would advantageously provide a simple, effective, and sanitary system for quickly disconnecting the tube carrying the fluid to the patient. Further, it is advantageous that any fluid injection system be small, light, simple to use and manufacture, durable and sterile, all while providing the advantages of an easy disconnect between the injection system and the fluid feed tube.

Among the approaches taken for quick disconnect systems are those found in U.S. Pat. Nos. 5,545,143 and 6,017,328 to Fishell, which system includes a fluid source, a fluid delivery tube which has a small needle and a septum in the body of the assembly for receipt of a needle. The needle is in a support base. At a first end, it is in fluid connection with the fluid in the tube. At a second end, it is designed to pierce a septum and deliver the fluid through a body and into a cannula. The cannula is inserted subcutaneous into the patient for delivery of the fluid into the patient. Such a system may generally be described as a "needle and septum" delivery system. The septum is integral with the main body and able to be repeatedly pierced, being self-sealing following the removal of the needle.

There are drawbacks to the devices illustrated in the referenced Fishell Patents and in the prior art in general. These drawbacks include the vertical injection of the fluid into the body of the system. Such an orientation provides unnecessary and unwanted height to the injection system. Ideally, an injection system should be almost flush with the skin of the patient. This "low profile" would allow, for example, loose fitting clothing to be worn during injection if the fluid delivery tube would be able to lay flush with the skin of the patient as it enters the body of the fluid injection system.

Thus, it is seen there are advantages to a fluid injection system with a low profile and a disconnect at the assembly. Such advantages should include a low profile with a quick and easy to use disconnect assembly that may be a needle and septum type disconnect assemble.

OBJECTS OF THE INVENTION

It is the object of this invention to provide for a low profile infusion assembly which is simple to manufacture and use and provide quick affective disconnect of the fluid feed line at body of the assembly.

SUMMARY OF THE INVENTION

Applicants' provides for these and other objects in a system for the subcutaneous delivery into the body of a patient of a fluid from a remote vessel or reservoir, the system comprising: main assembly and placement member having a needle thereon; a delivery tube for carrying a fluid, the delivery tube attached at a near end to the remote fluid containing vessel and at a removed end having a rotating member engagement device, which includes a needle; and a main assembly including a body having a cannula depending therefrom and a rotating member, the rotating member including an engagement arm for rotating with respect to the body from a first position providing axle alignment of the engagement arm of the rotating member with the cannula to a second position, the second position providing fluid communication between the removed end of the engagement arm on the rotating member in the cannula when the delivery tube is attached thereto.

BRIEF DESCRIPTION OF THE DRAWINGS

FIGS. 1H and 2 provide a cross section elevational view and perspective view, of the invention with the fluid connector attached thereto and in a "down" position, that is, the position that the invention would be in when in use, that is, delivering fluid from a remote vessel (not shown) into the body of a patient.

FIG. 9 illustrates a cross sectional view of a first embodiment of Applicant's present invention with the fluid connector attached thereto and in a "down" use position.

DETAILED DESCRIPTION OF THE PREFERRED EMBODIMENTS

Figure 1A:
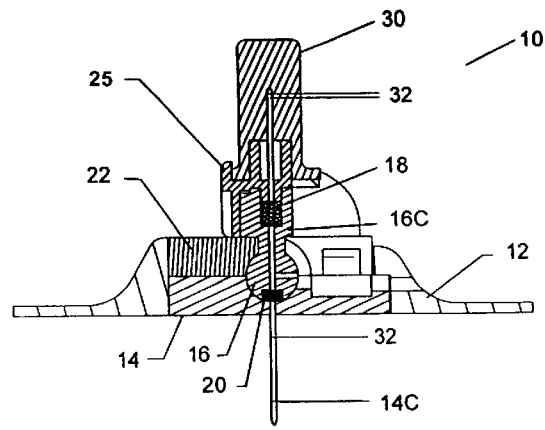
FIGS. 1A through 1G represent various views of a first embodiment of Applicant's invention in the condition for placement on a patient, that is, with handle and needle as part thereof.

The above description sets forth some of the objectives of Applicant's unique fluid injection assembly (10) set forth in FIGS. 1A–20C below. We will now turn to these figures for the details of the fluid injection assembly (10) of Applicant's present invention and to appreciate the many advantages of the invention.

Turning now to FIGS. 1A–1H and FIG. 2; the main components of Applicant's fluid injection assembly (10) are set forth, and in particular, show the manner in which these elements include structural components cooperating together in providing effective delivery of a fluid into the body of the patient. As a matter of background, and prior to an introduction of details of Applicant's present invention, the reader is advised that most fluid injection systems are provided with structure for initially implanting the system into the body. By that, Applicant means that a fluid injection system typically has a cannula descending from the fluid injection system body, the cannula being a soft, flexible tube, and it is necessary to provide some stiffness to that soft flexible cannula, usually a sharp needle to sleeve within the cannula before the cannula is ready for placement through the skin of the patient. A cannula alone does not have the rigidity to puncture the skin of the patient and thus, most fluid assembly systems typically provide for a device and a method including a sharp pointed needle insertable within the cannula and through the body of the injection system so the unit may be placed on the skin of the patient with the cannula around a sharp needle and inserted under the skin. Once the cannula is properly placed, the needle can be withdrawn and discarded and the system is now ready for receipt of a fluid, borne through a delivery tube, the delivery tube engageable with the body of the injection system. The injection system, having been thus "installed" onto the body of the patient can then remain for many days while the delivery tube may be periodically disconnected as the patient wishes to move about.

Now, with this background, Applicant will address further details of the novel fluid injection assembly (10) as initially set forth in FIGS. 1A–1H. It is immediately appreciated with reference to these figures that the main components of Applicant's fluid injection assembly (10) may contain: a main assembly body (12); a base (14); a rotating, pivoting or ball joint (16) (the ball joint containing a first septum (18) and a second septum (20)); a cover (22); a fluid connector (24) (see to FIG. 1H the fluid connector including a needle (26) and a feed tube (28)); a plug (25); and a handle (30) (including an insertion needle (32)).

FIGS. 1A through 1G, illustrate Applicant's fluid injection assembly (10) ready for its initial emplacement into the skin. Therefore, FIGS. 1A–1G illustrate Applicant's fluid injection assembly as it includes handle (30), having an insertion needle (32), the insertion needle (32) sheathed inside a cannula (14C) to provide the necessary rigidity with the sharp pointed end (32A) of needle (32) for insertion into and through the skin of the patient. After placement, handle (30) is withdrawn from the rest of fluid injection assembly (10) and discarded. At this point, fluid injection assembly (10) is capable of receiving fluid connector (24) and the fluid, from a remote reservoir (not shown), which as set for in more detail below, will be carried into the body of the patient.

Applicant's fluid injection assembly (10) includes a main body assembly (12) whose functions include locating other components of the assembly and providing a platform for those other components to mount and cooperate thereupon and with one another as set forth in more detail below. This particular function of main assembly body (12) may be appreciated with reference to FIG. 1A, which illustrates how a number of other components are joined to the main body assembly (12).

Cooperating with the main assembly body (12) is base (14) into which seats a rotating or ball joint (16) over-lain with a cover (22). More specifically, a base (14) insertable beneath the main assembly body (12) and a cover (22) cooperating with the base (14), "sandwich" or enclose rotating ball joint (16), the ball joint including a first septum (18) and a second septum (20), the first septum for receipt of a needle (26) borne on the fluid connector (24) for delivery of fluid from a remote reservoir into the ball joint (16) then through the cannula (14C) and into the body of the patient (see FIG. 1H).

Figure 1B:
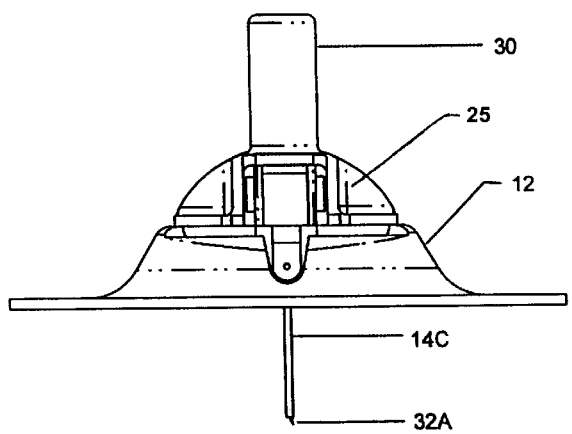
Figure 1C:
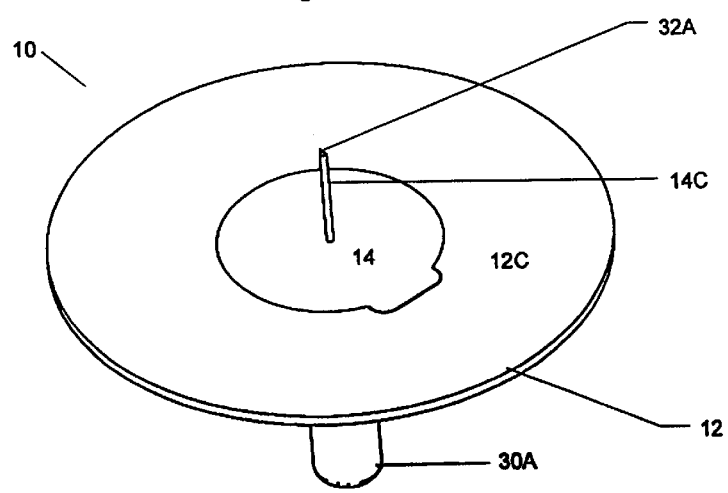
Figure 1D:
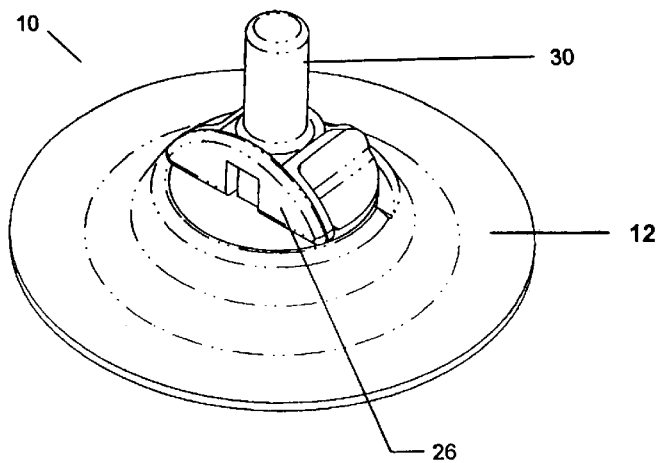
Figure 1E:
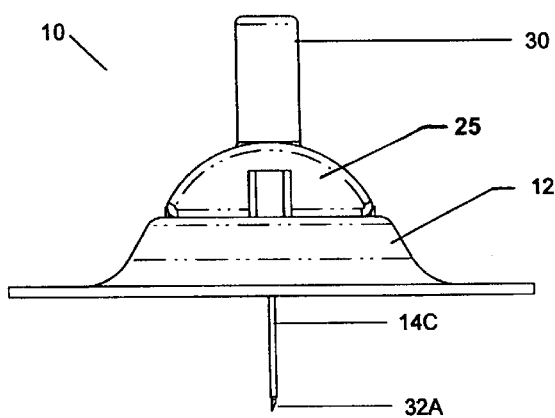
Figure 1F:
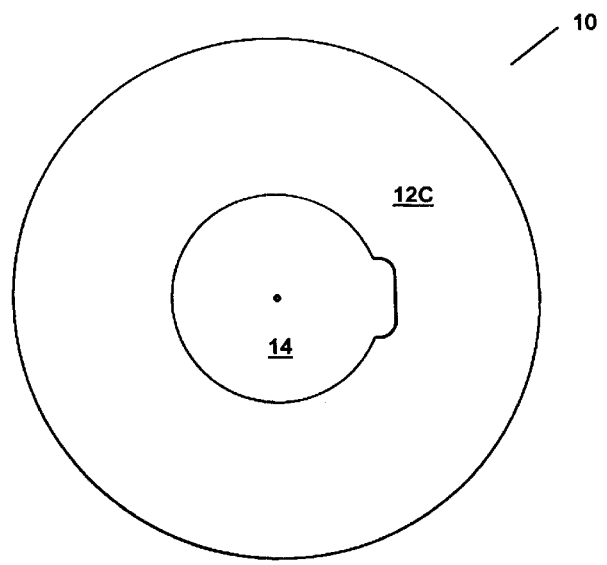
Figure 1G:
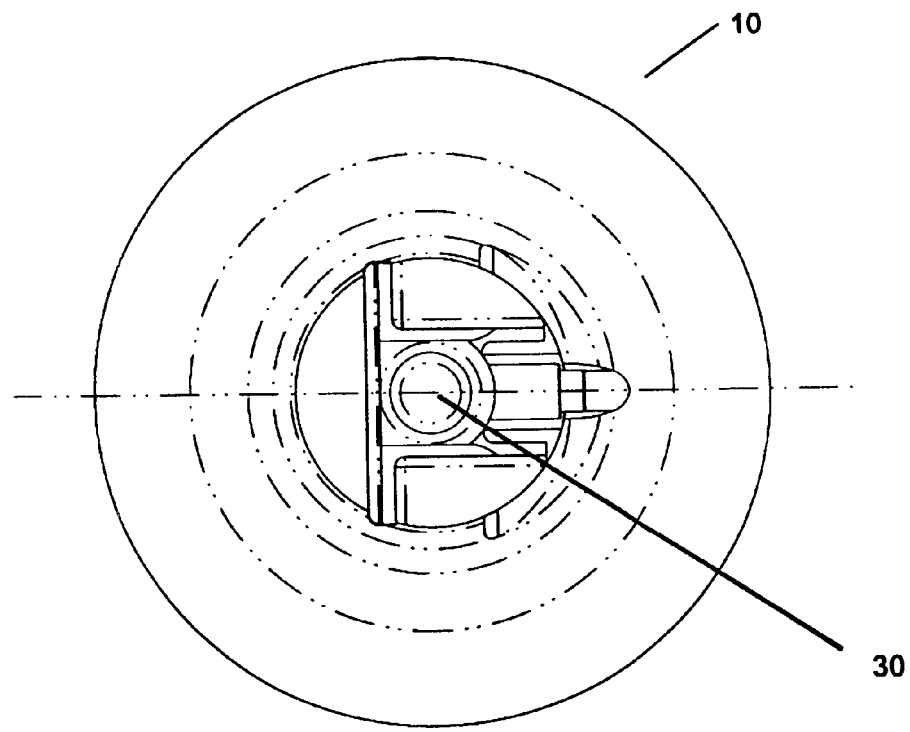
Figure 1H:
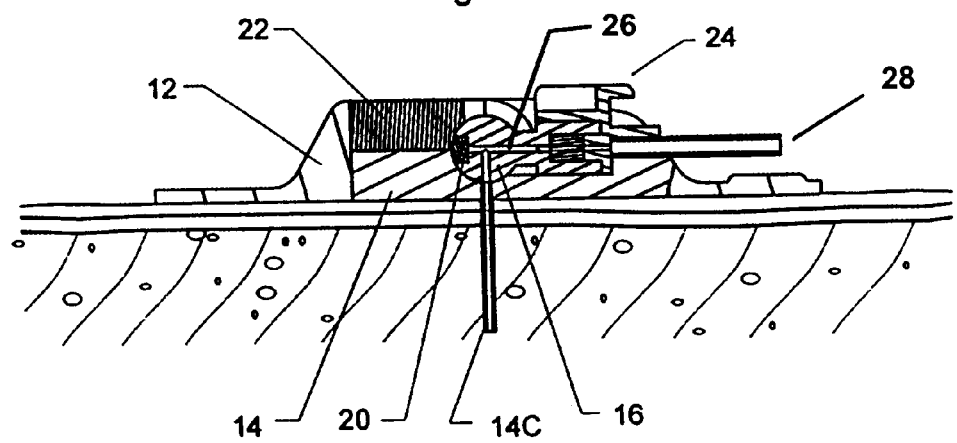

It should be appreciated that FIGS. 1A through 1G and FIG. 2, illustrate assembly (10) in the configuration that allows the initial insertion and placement of the assembly upon the body of the patient. That is, in its configuration including handle (30) having an insertion needle (32). More specifically with the reference to FIG. 1A it is seen that handle (30) includes insertion needle (32), which needle penetrates the first septum (18) and second septum (20), continues through cannula (14C) until just the pointed-tip (32A) of insertion needle (32), extends beyond the cannula (14C), as best appreciated with referenced FIG. 1E. Also appreciated with referenced to FIGS. 1H is the low profile of the main assembly body (12). Further, it is seen, especially with reference to FIG. 1A, how plug (25) engages ball joint (16); more specifically, an engagement arm (16C) thereof, and acts as a guide for receipt of handle (30) there through. Further, it is appreciated how ball joint (16) is sandwiched and rotatable, here about 90°, between base (14) and cover (22).

Further details of each of the separate components of Applicant's injection system will be set forth in more detail below following which we will return to the drawings of the assembled device.

Figure 3A:
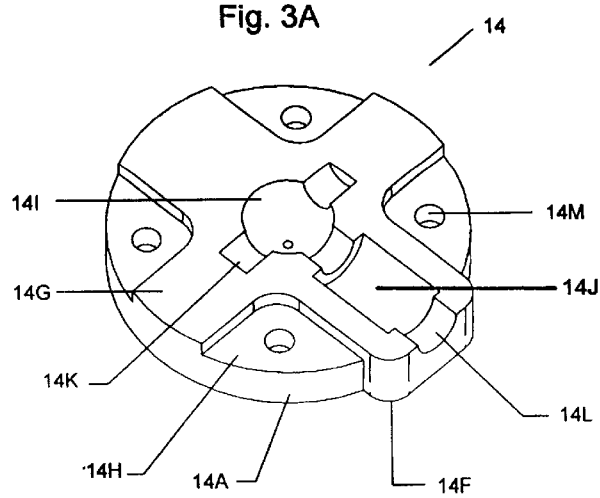
FIGS. 3A through 3G represent various views of the base of a first embodiment of Applicant's invention.
Figure 3B:
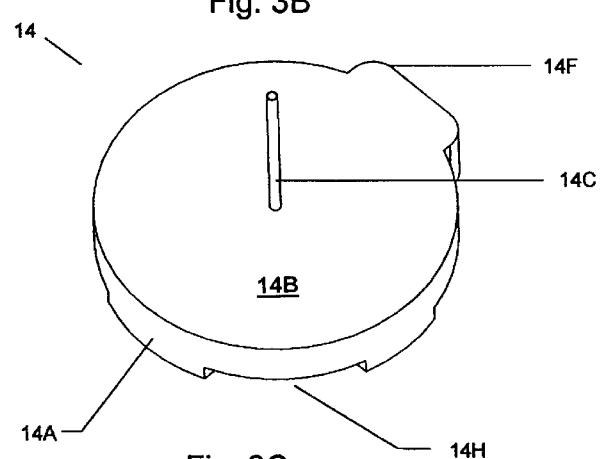
Figure 3C:
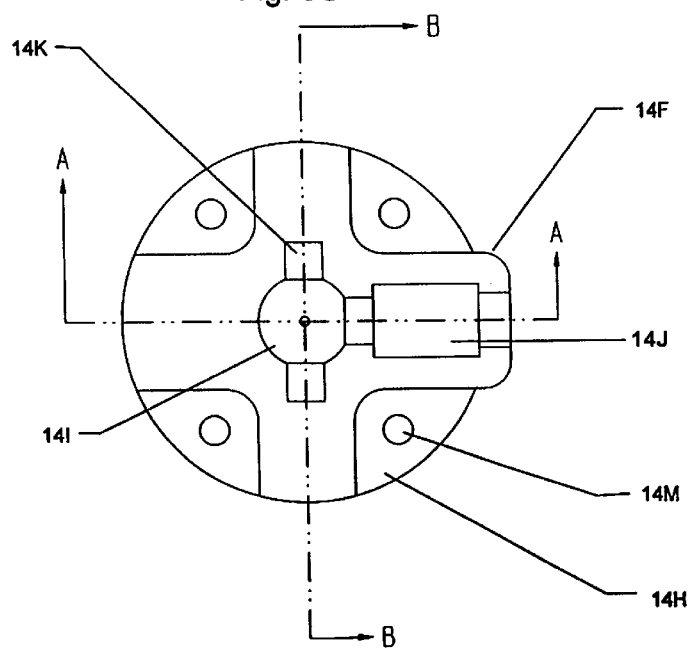
Figure 3D:
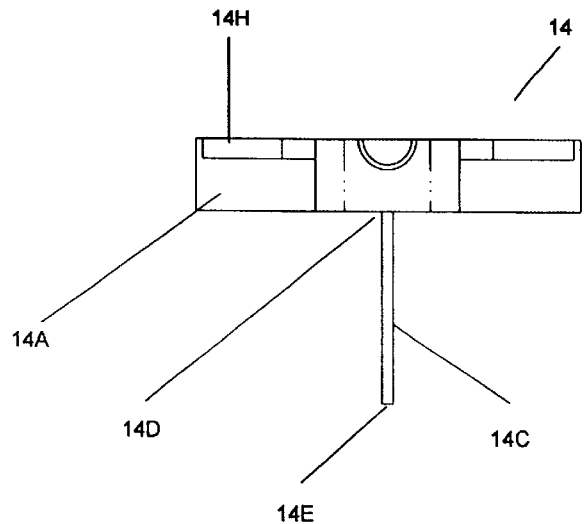
Figure 3E:
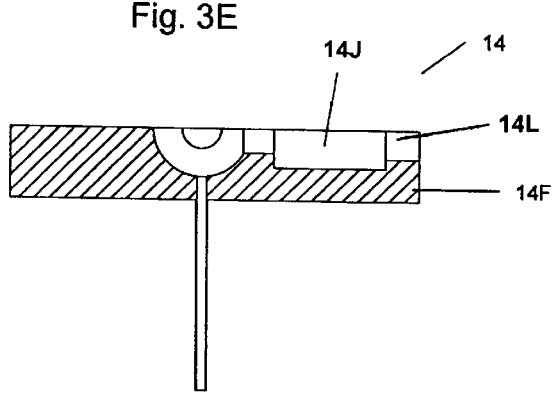
Figure 3F:
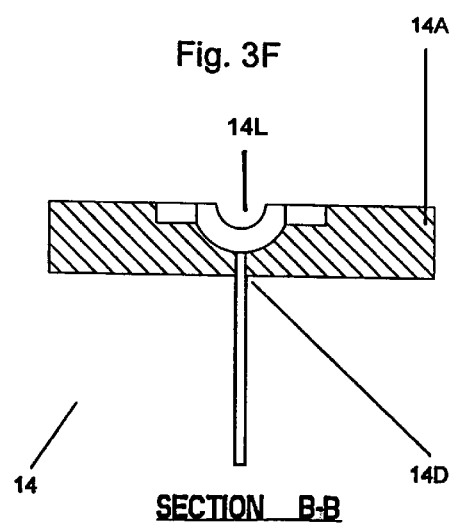
Figure 3G:
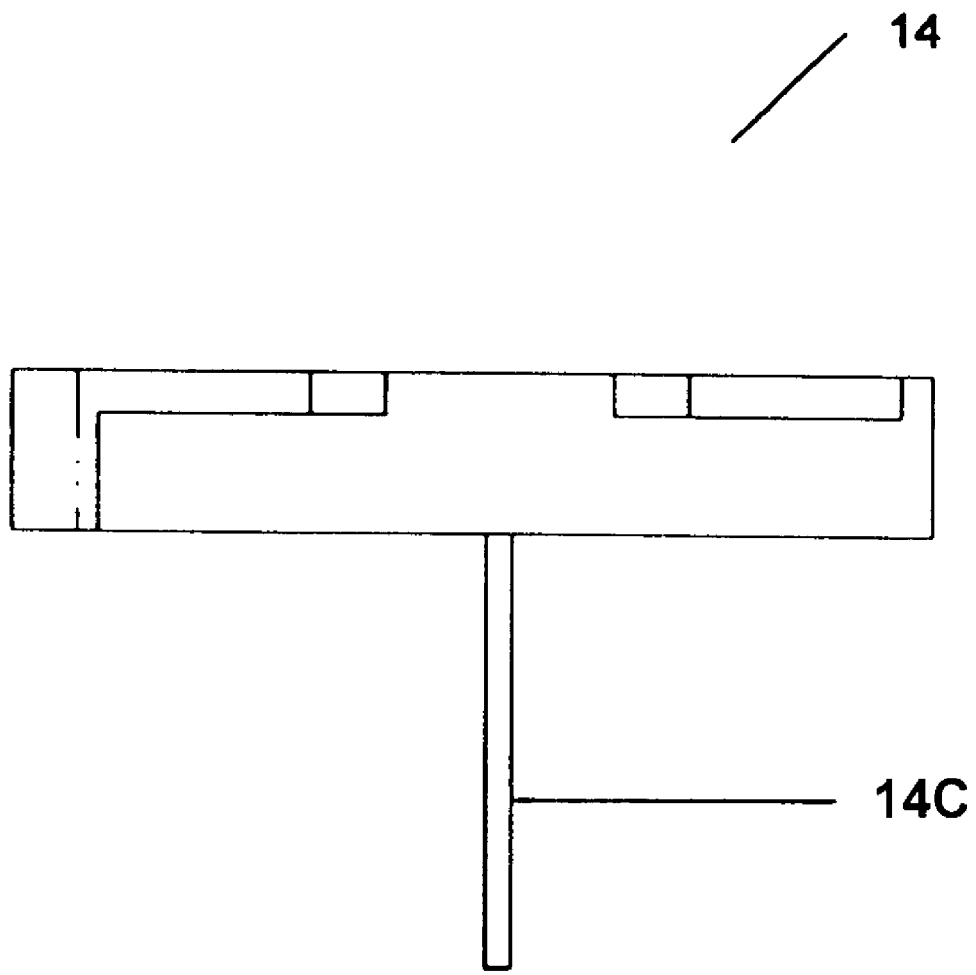
Figure 4A:
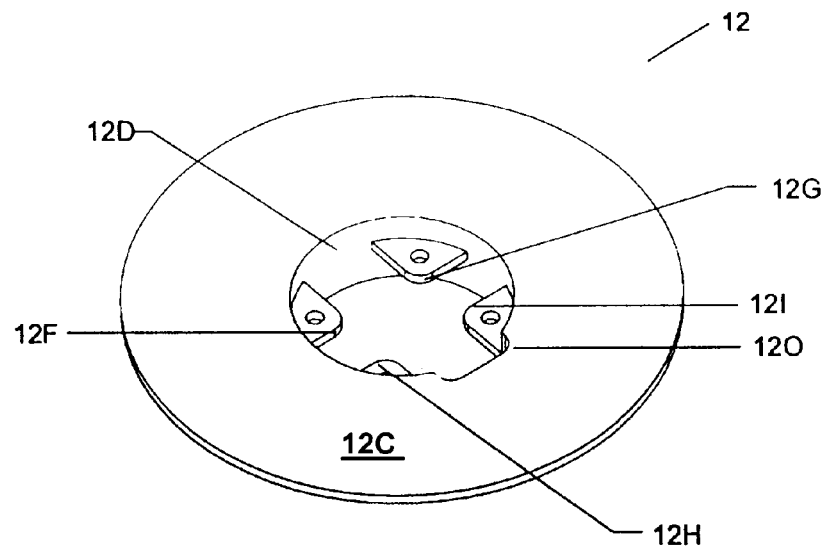
FIGS. 4A through 4F illustrate various views of the main assembly body of a first embodiment of Applicant's present invention.
Figure 4B:
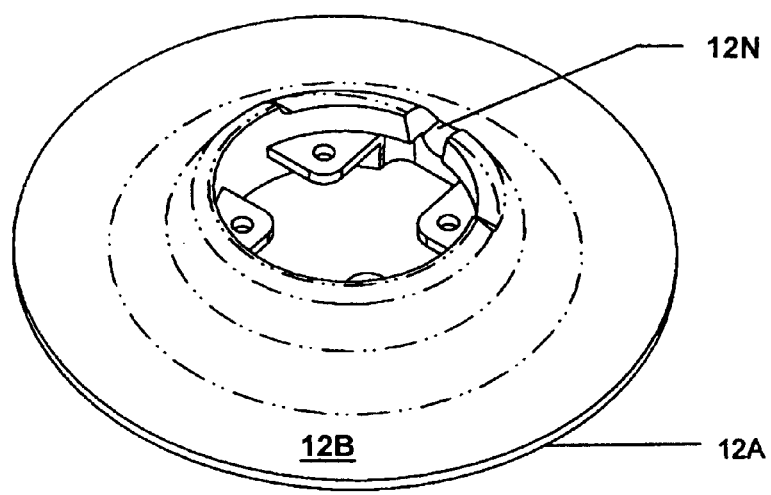
Figure 4C:
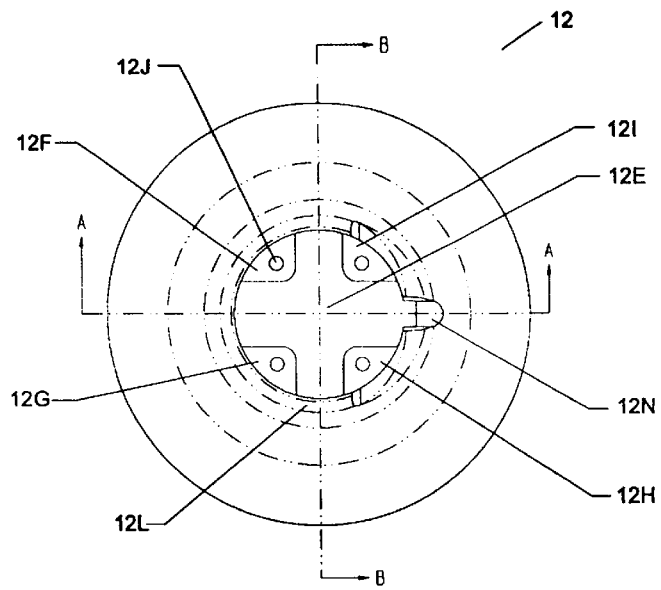
Figure 4D:
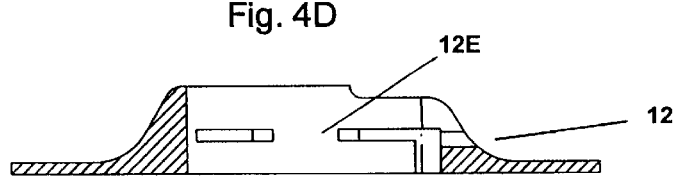
Figure 4E:
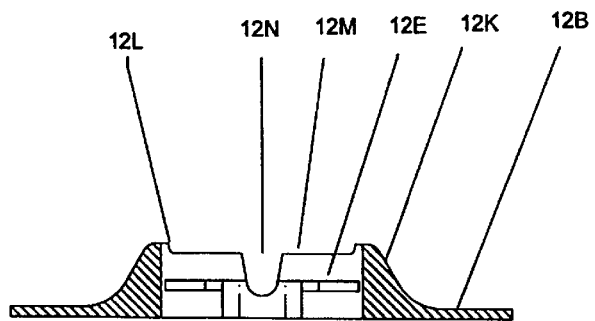
Figure 4F:
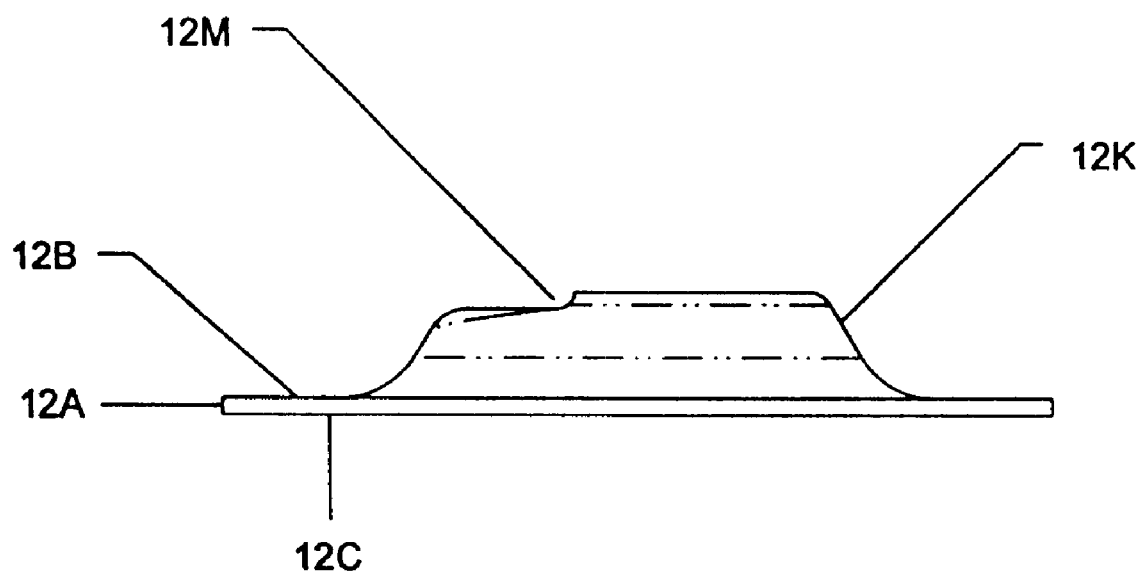
Figure 5A:
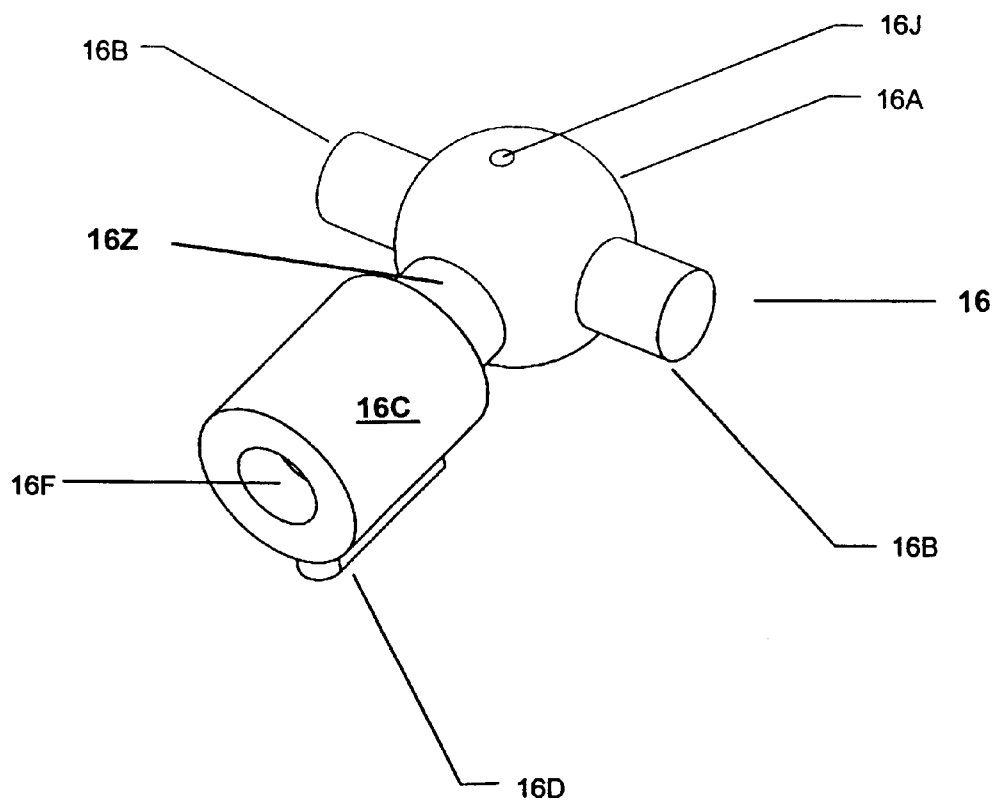
FIGS. 5A through 5G illustrate various views of the pivoting joint of a first embodiment of Applicant's present invention.
Figure 5B:
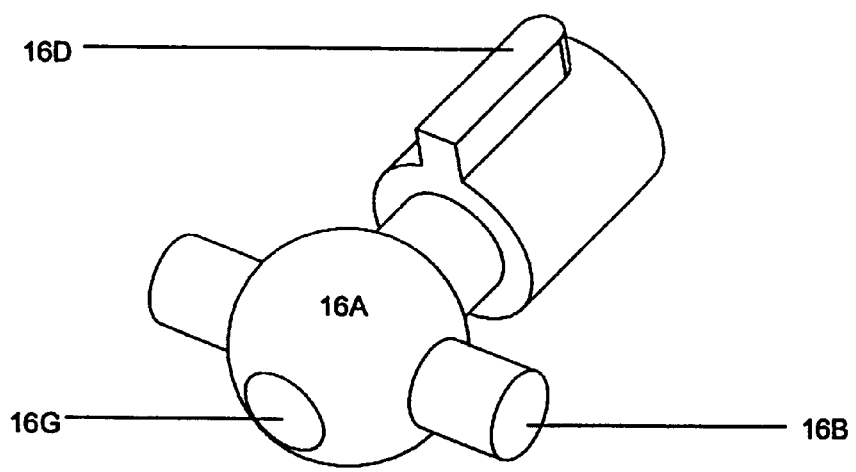
Figure 5C:
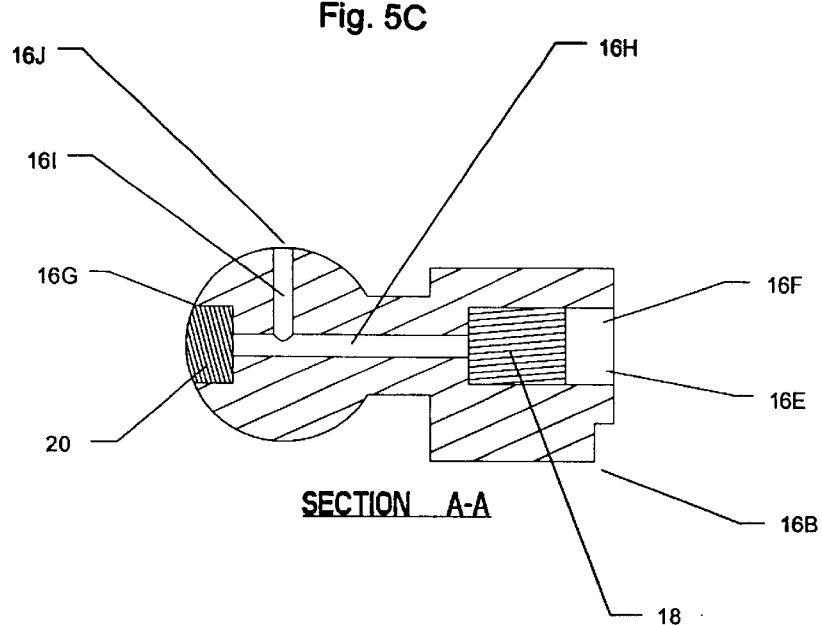
Figure 5D:
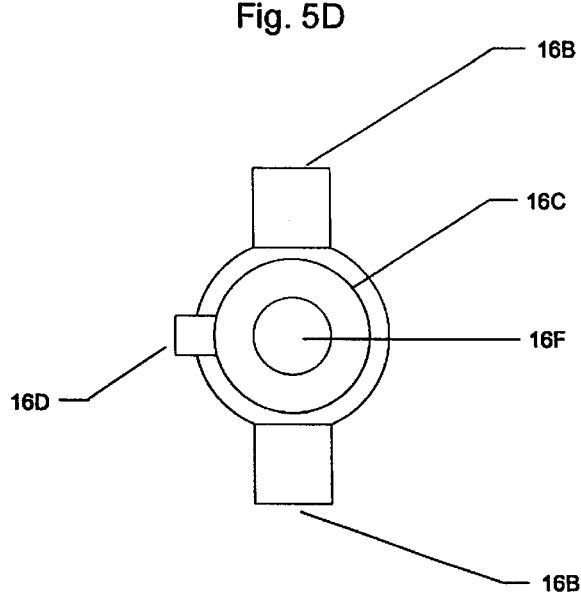
Figure 5E:
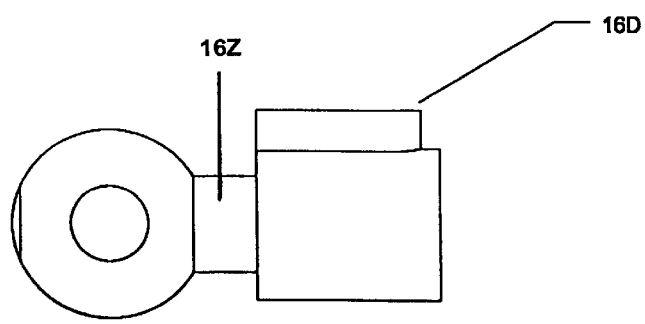
Figure 5F:
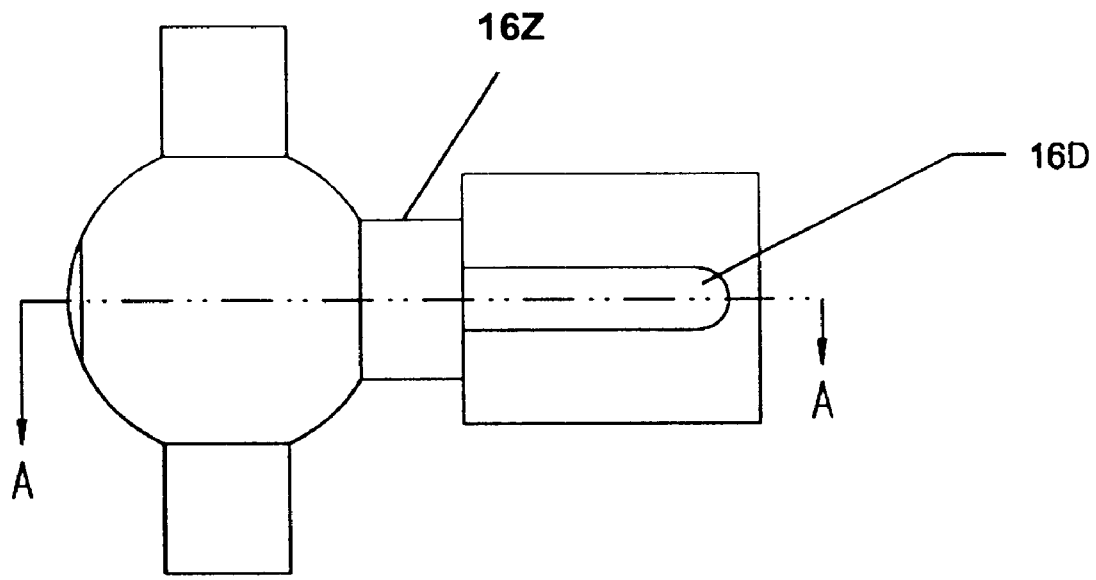
Figure 5G:
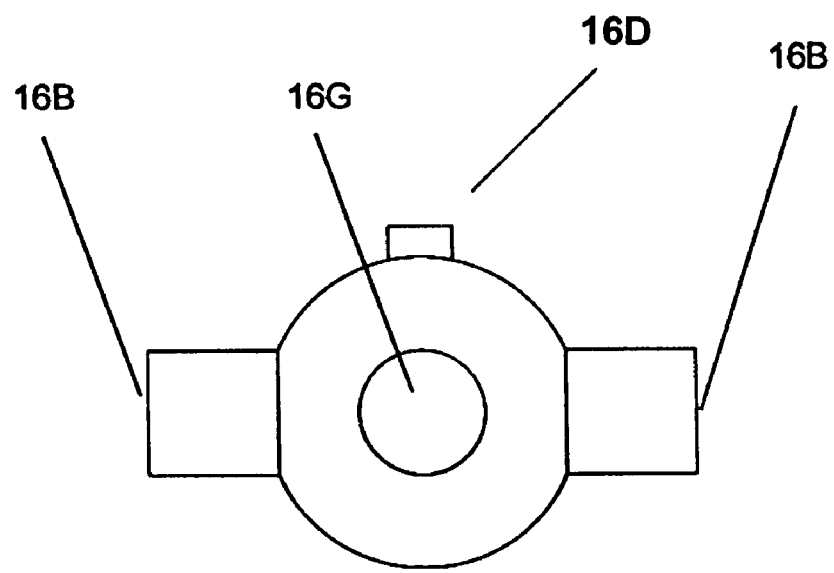

FIG. 3A–3G illustrate a base (14) whose function is to locate ball joint (16) within main assembly body (12) and to provide engagement with the ball joint and a vertically oriented cannula (14C), depending from a bottom surface (14B) of the base. The base is also seen to have perimeter walls (14A) describing a generally circular structure having a bottom surface (14B) and a top surface (14G). Descending from the bottom surface (14B) is the aforementioned cannula (14C) which is attached to the base (14) near the center of the bottom surface (14B) at a near-end thereof, the cannula (14C) being a cylindrical, hollow sheath structure having a removed-end (14E) the removed end having a conical cross section (See FIG. 3D). The function of the cannula (14C) is to carry a fluid received from the ball top surface (14G) thereof which cutouts mimic the outline of the ball joint (16). Additionally, as best seen with reference to FIG. 3A, cutouts (14H) are four in number and located around the perimeter of top surface (14G) which mimic the outline of and are capable of enclosing legs (12F, 12G, 12H, and 12I) of main assembly (12) (see FIG. 4A). Base (14) is also seen to include a boss (14F) (See FIG. 3B) along the perimeter walls, the boss (14F) for seating into notched-portion (12O) of main assembly body (12) (see FIG. 4A). Reference is made to FIG. 3A where it is seen that within cutout (14H) of the bottom (top) surface of the base, there is located apertures (14M) for receiving the four receiving legs (22 E, F, G, and H) of cover (22) (see FIG. 6A). Thus, it is seen that ball joint seat (14I) is more particularly designed to receive ball joint (16), providing as part thereof ball joint engagement arm recess (14J) for receipt of ball joint main body (16A) thereinto, support on recesses (14K) for receipt of support arms (16B) therein (see FIG. 5A) and engagement arm recess (14L) for receipt there into of engagement arm (16C) of ball joint (see FIG. 5A). Moreover, it is seen with reference to FIGS. 3A and 3C that cutouts (14H) are shaped to receive legs (12 F, G, H, and I) of the main assembly body (12) to locate the base within the main assembly body (12) as set forth in more detail below.

Turning now to FIGS. 4A through 4F, a main assembly body (12) is described, the purpose of which is to provide a structure on which to locate the other assemblies of Applicant's fluid injection assembly (10), and further, to provide a bottom surface (12C) attachable through an adhesive to the skin of a patient. More specifically, main assembly body (12) is seen to be generally disc-shaped and having a low profile (see FIG. 4D). The main assembly body (12) is typically, approximately 0.8-inches in diameter with a height of about 0.29-inches.

Applicant's novel design has achieved both a "low profile" (a height lower than approximately 0.30-inches) and a small "footprint" which has a radius of about 0.8-inches and a surface area of about 0.55 square inches. This provides what is generally described as a "small footprint." Applicant's device provides a width-to-height ratio of approximately 2.75 to 1 (or lower), providing generally what is to be described as "low profile." Further, it is seen that the main assembly body (12) has a perimeter (12A) and a top surface (12B), the top surface (12B) including raised walls (12K), including walls (12D), defining a central opening (12E), into which is inserted from the under side thereof, the afore-described base. The main assembly body (12) includes legs (12 F, G, H, and I) having apertures (12J) therein, which legs receive cutouts (14H) of the base when the base is inserted upwards through the bottom of the main assembly body (12) into central opening (12E) with apertures (12J) aligned with apertures (14M) of the base, and with notched-portion (12O) of main assembly body (12) for receipt of boss (14F) of base (14). With base (14) properly inserted into central opening (12E) from below main assembly body (12), cutouts (14H) and legs (12F, G, H and I) will seat together and cannula (14C) will be seen to project below main assembly body (12), as is best seen with reference to FIGS. 1A and 1B main assembly body 12 includes upper lip (12L) and fluid connector cutout (12M) for engaging the fluid connector cover and also feed tube engagement cut out (12N). In this configuration, it can be seen that a pivoting or ball joint (16), as more specifically described in FIGS. 5A–5E, can be placed in ball joint seat (14I) of base (14), as more specifically set forth in FIG. 1B. We will now turn to the description of Applicant's novel rotating or ball joint (16) and its structure.

Figure 6A:
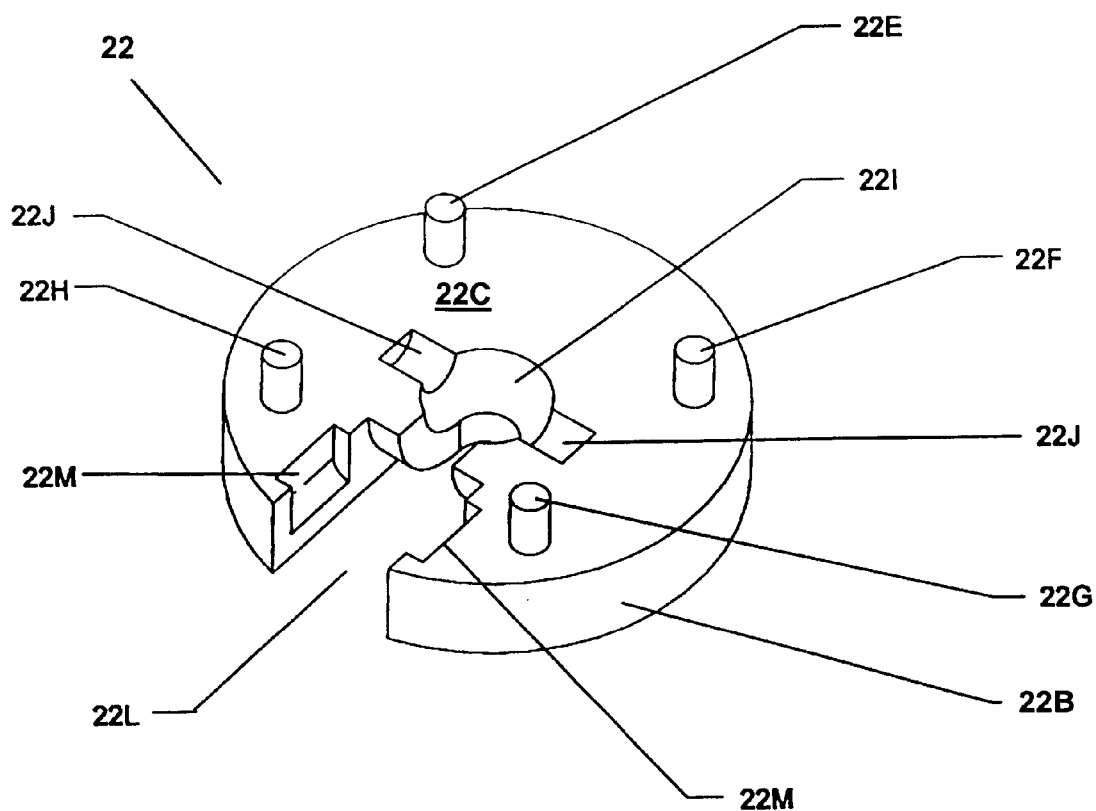
FIGS. 6A through 6H illustrate various views of the cover of a first embodiment of Applicant's present invention.
Figure 6B:
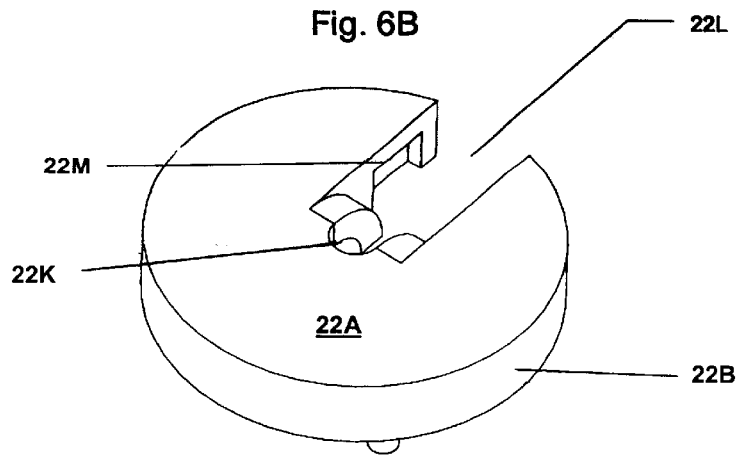
Figure 6C:
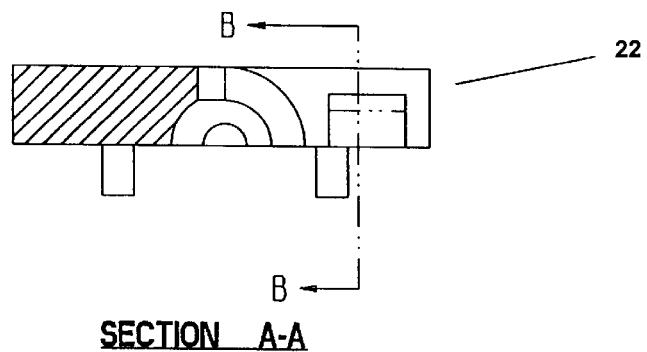
Figure 6D:
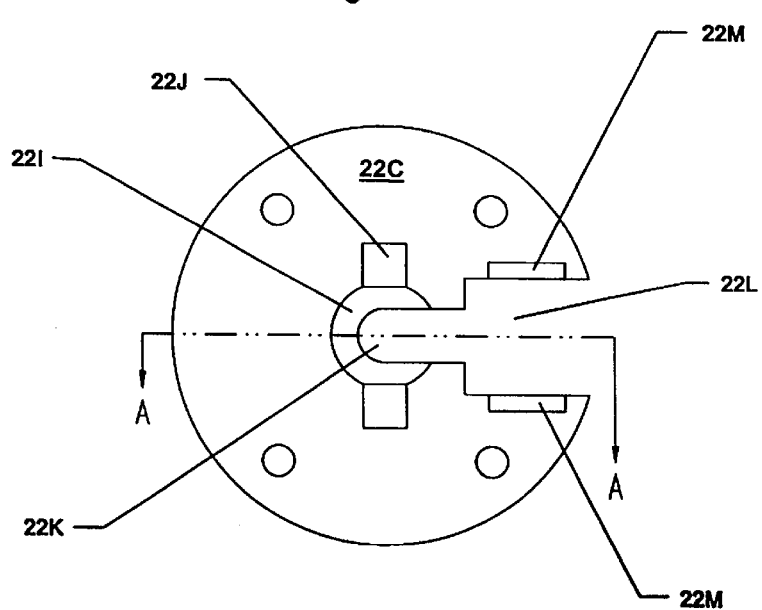
Figure 6E:
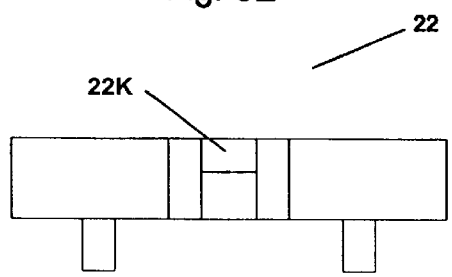
Figure 6F:
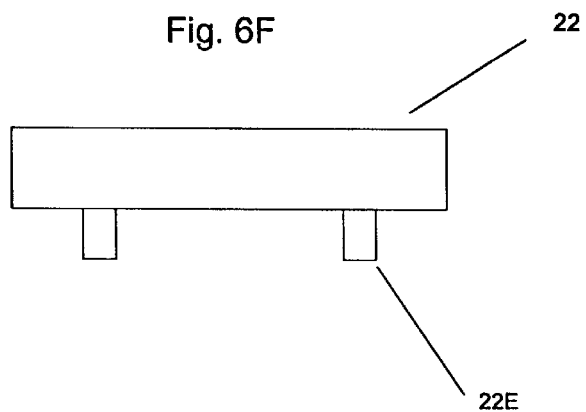
Figure 6G:
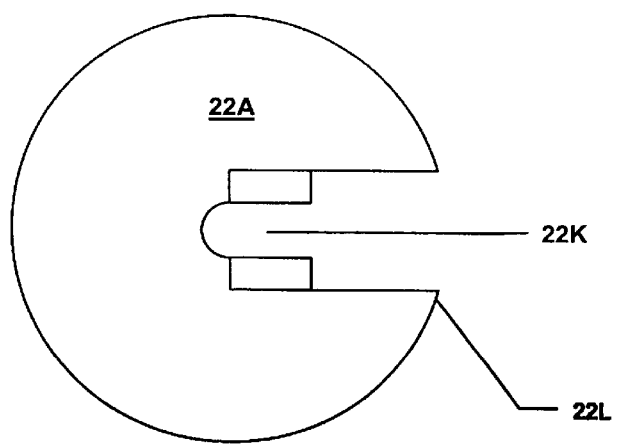
Figure 6H:
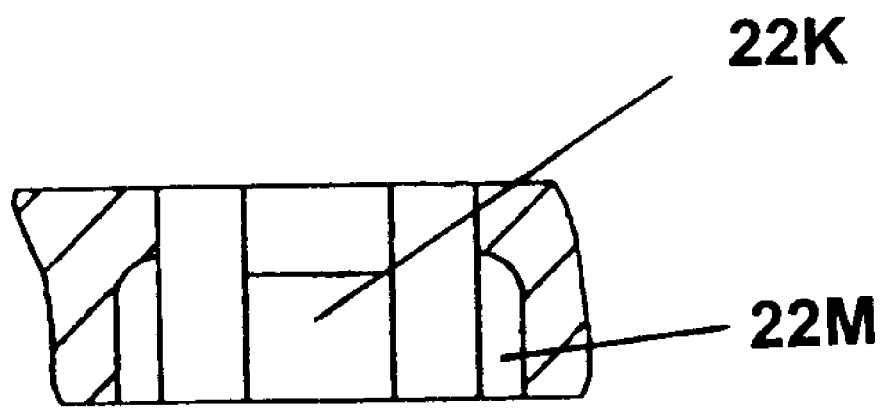

Turning now FIGS. 5A through 5G, the structure and components of Applicant's unique ball joint may be appreciated. Ball joint (16) typically includes at least partly a spherical main body (16A) which is seen to have projecting therefrom cylindrical, opposed support arms (16B) and, on an axis perpendicular to the axis described by the support arms (16B); this is seen to have an engagement arm (16C). Support arms (16B) support the ball joint within support arm recesses (14K) of the base (14) and also, within support arm cutouts (22J) of cover (22), as seen in FIG. 6A. Engagement arm (16C) is also seen to have a ball joint guide member (16D) on a portion thereof This will be seen to provide engagement with both the plug (25) and when the plug (25) is removed, with the fluid connector (24) (see ball joint guide notch cutout (24D) in FIG. 7A). Also, as seen with reference to FIG. 5C, the interior of ball joint (16) includes a central channel or bore (16E) having an enlarged or cut out first end (16F) and an enlarged or cut out second end (16G) and a central portion (16H) between the first end and the second end. Diagonal to the central bore (16E) and connected with the central portion (16H) thereof is a feed channel bore (16) which communicates with the surface of the body of the ball joint (16) at aperture (16J). Further, it is seen that the first septum (18) seats recessed within enlarged or cut out first end (16F) and second septum (20) seats snugly within enlarged second end (16G). There is a neck (16Z) between ball joint main body (16A) and engagement arm (16C).

FIGS. 6A through 6H illustrate details of Applicant's cover (22). Applicant's cover (22) is generally cylindrical in shape and designed to fit in the central opening (12E) of the main assembly body (12), as seen in FIG. 1A, such that legs (22 E, F, G, and H) are insertable through apertures (12J) in each of main assembly body legs (12 F, G, H, and 1) and further, such that legs (22 E, F, G and H) extend through the main assembly body legs and into base (14) at apertures (14M) in the base. Thus, legs (12 F, G, H, and I) of main assembly body (12) and legs (22 E, F, G, and H) of cover (22) engage one another and base (14) to sandwich ball joint (16) within central opening (12E) and between the base (14) and the cover (22) as best seen in FIG. 1A.

Having discussed a function of cover (22), we now return to the details thereof. More specifically, it seen that cover (22) is generally disc-shaped and includes a top surface (22A) and perimeter walls (22B), the perimeter walls (22B) being designed to engage the walls defining central opening (12E). Cover (22) is also seen to have a lower surface (22C). Projecting from the lower surface (22C) are the aforementioned cylindrically legs (22 E, F, G, and H) dimensioned to engage both the apertures (12J) of the main assembly body (12) and apertures (14M) of the base. Cover (22) is also seen to have defined on a lower surface thereof, a recessed portion or ball joint seat (22I), the ball joint seat (22I) including recesses for ball joint support arm cutouts (22J) and ball joint engagement arm cutout (22L). The lower surface (22C) of the cover also includes a neck cutout (22K), for allowing the ball joint (16) to rest in an up position (see FIG. 1A), and a ball joint seat (22I) where a ball joint (16) may rest as is apparent from viewing FIG. 1A and 1H. Moreover, it is seen that ball joint seat (22I) is configured such that the ball joint (16) may lay in a plane parallel to that of the cover (a "down" position) (see FIG. 1H) and thus, rest with the engagement arm (16C) of the ball joint (16) in ball joint engagement arm cutout (22L) or, the ball joint (16) may be rotated to a position perpendicular thereto, as is illustrated in FIG. 1A, such that the engagement arm (16C) rotates out of engagement arm cutout (22L) and stands perpendicular to top surface (22A). Last, it is seen that cover (22) includes fluid connector locking boss coves (22M) for lockingly link maintaining the fluid connector in a down or "use" position as set forth in more detail below and with reference to FIG. 9.

FIGS. 7A through 7G illustrate Applicant's fluid connector (24). The function of fluid connector (24) is to provide a means for delivery of a fluid to the remaining elements of the fluid injection assembly (10) to ultimately reach the patient through the cannula (14C). The general method of doing so is to connect a feed tube (28) bearing a fluid therein to a needle (26) having a removed end (26A). The needle (26) will penetrate first septum (18) to deliver a fluid into the central bore (16E) of the ball joint (16) for delivery, through feed bore (16I) to cannula (14C) as set forth in FIG. 1H. Note that the first septum is "self sealing" such that when needle (26) is removed, for example, temporarily when a patient wishes to leave his or her bed, no fluid that has left the needle and is in the injection assembly will escape.

Understanding the general function of fluid connector (24), reference is now made to FIGS. 7A through 7F for more details of the structure of the fluid connector (24). Fluid connector (24) is seen to include a fluid connector body (24E), the body having a semi-circular shape cover (24A) defining a cover perimeter (24B). Projecting from the cover (24A) are walls defining an engagement arm cutout (24C), these walls contiguous with a ball joint guide cutout (24D). When the fluid connector is engaged to the ball joint so that needle (26) penetrates the first septum, engagement arm cutout (24C) will partially enclose the engagement arm such that ball joint guide notch (16B) is seated snugly within ball joint guide cutout (24D). It is also seen that fluid connector (24) includes, on walls perpendicular to cover (24A), a pair of oppositely disposed locking bosses (24F) for locking engagement with fluid connector boss coves (22M) of cover (22) when fluid connector is in a down or use position, as set forth in FIG. 9. There are a number of advantages to Applicant's unique fluid engagement means, which consists of a pair of locking bosses (24F) releasably engaging fluid connector boss coves (22M). First, there is the tactile "feel" that the patient will get when the bosses "pop" into the coves. Second, there is the audible "click" that occurs when the bosses "pop" into the coves. Both of these sensory signals are important to assure the patient that the fluid connector (24) is locked on to the assembly (12) and locked down to ensure communication with the cannula (14C)—that is, to ensure that the fluid flowing through the delivery tube is in fact flowing through the cannula (14C) and into the patient. Such a recallable, positive lock down means also helps prevent accidental dislodging of the tubing. Further, the system of a ball guide cutout (24D) and ball joint guide (16D) provides for easy and effective alignment of fluid connector (24) to the engagement arm (16C) of the ball joint (16) to easily and positively affix the infusion tubing to the assembly via a keyed mating of the tubing to the ball joint (16). Note that Applicant's system removes the tubing from the main assembly (12) (by disconnecting at the infusion assembly) and that it does not leave a "tail" of delivery tubing as is found in prior art systems which provide disconnect spliced into the delivery tube itself, rather than at the removed end (that is, at the infusion assembly).

Figure 7A:
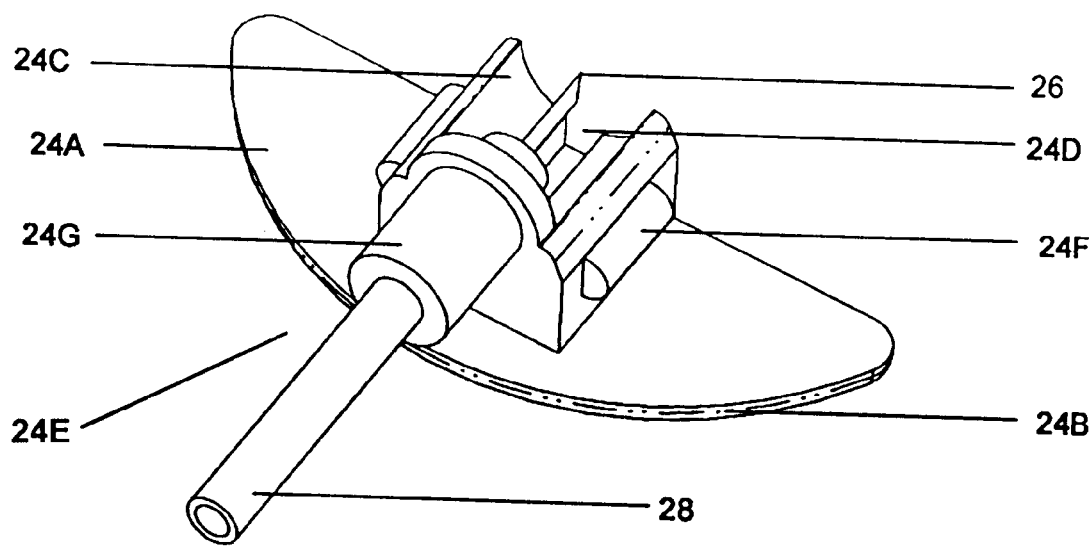
FIGS. 7A through 7G illustrate various views of the fluid connector of a first embodiment of Applicant's present invention.
Figure 7B:
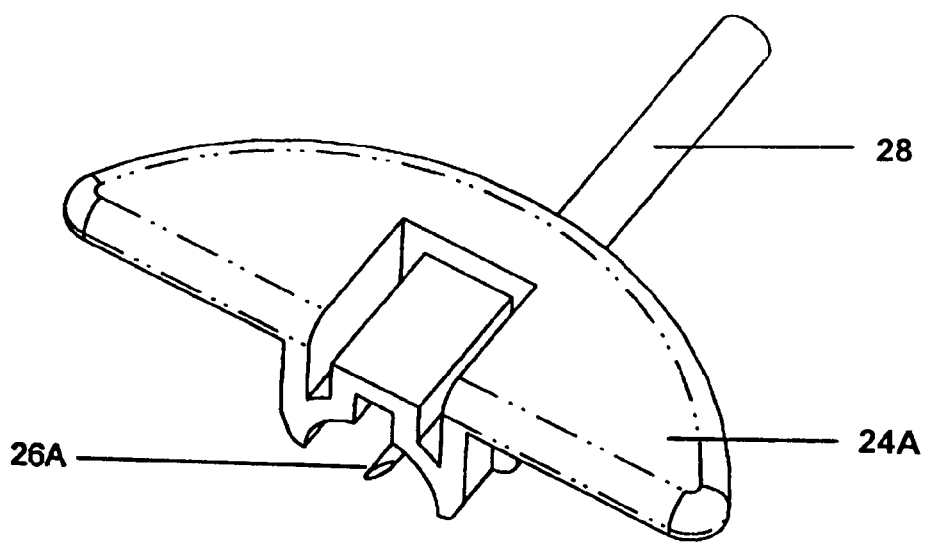
Figure 7C:
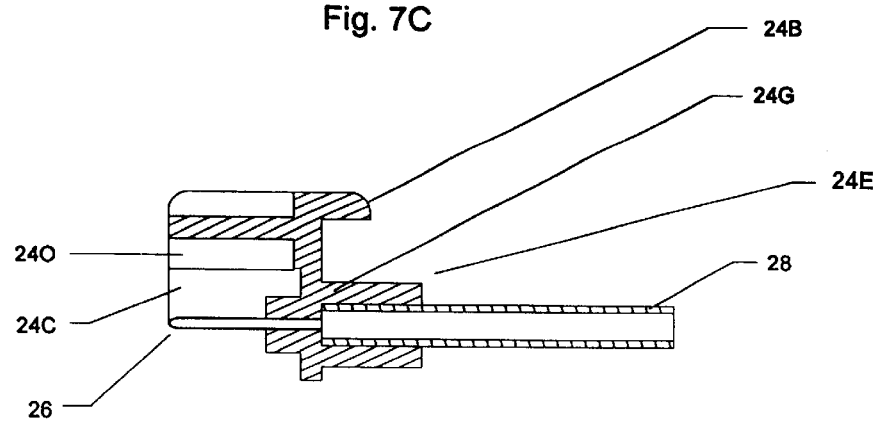
Figure 7D:
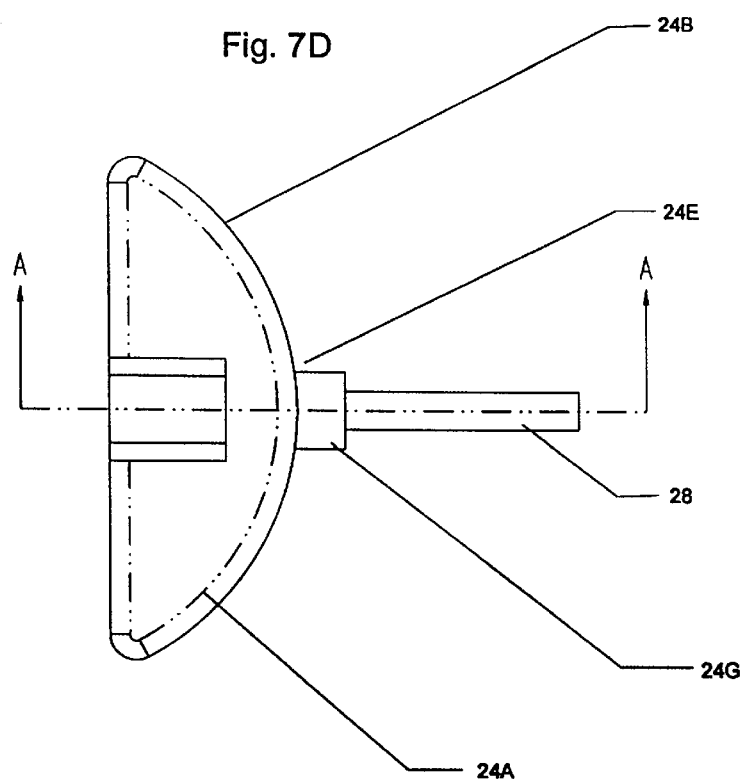
Figure 7E:
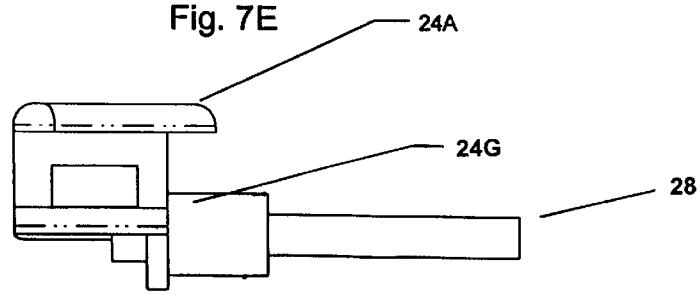
Figure 7F:
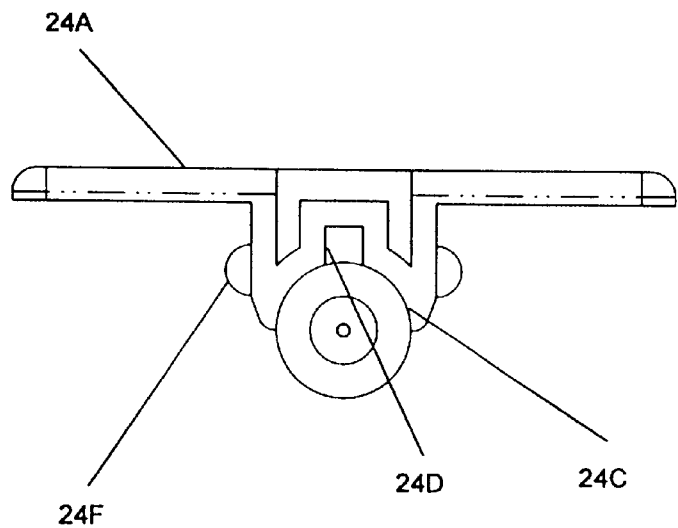
Figure 7G:
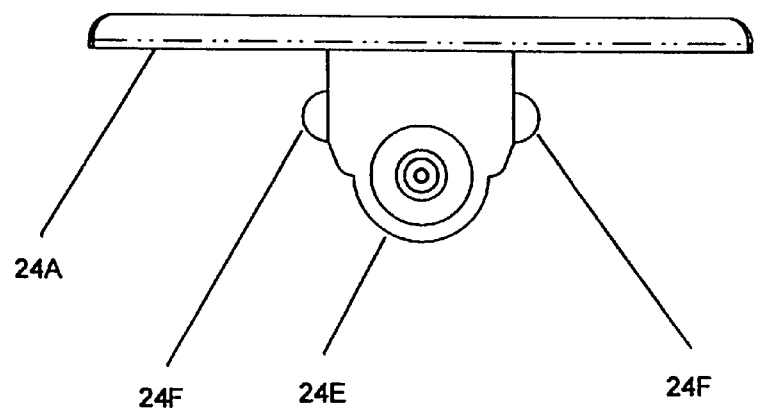

It is seen with reference to FIG. 7A and 7C that fluid connector body (24E) includes feed tube engagement portion (24G) to receive the end of feed tube (28) and further to provide a sealed mounting boss for needle (26). Thus, a function of fluid connector (24) is to provide means to receive the feed tube (28) in fluid tight relation and to mount needle (26) therein in a manner that will allow the needle (26) to align properly with the ball joint (16) and further, will allow the fluid connector to move down and lock as it is joined to the ball joint (16) in a down, folded or use position, as seen in FIG. 9.

Figure 8A:
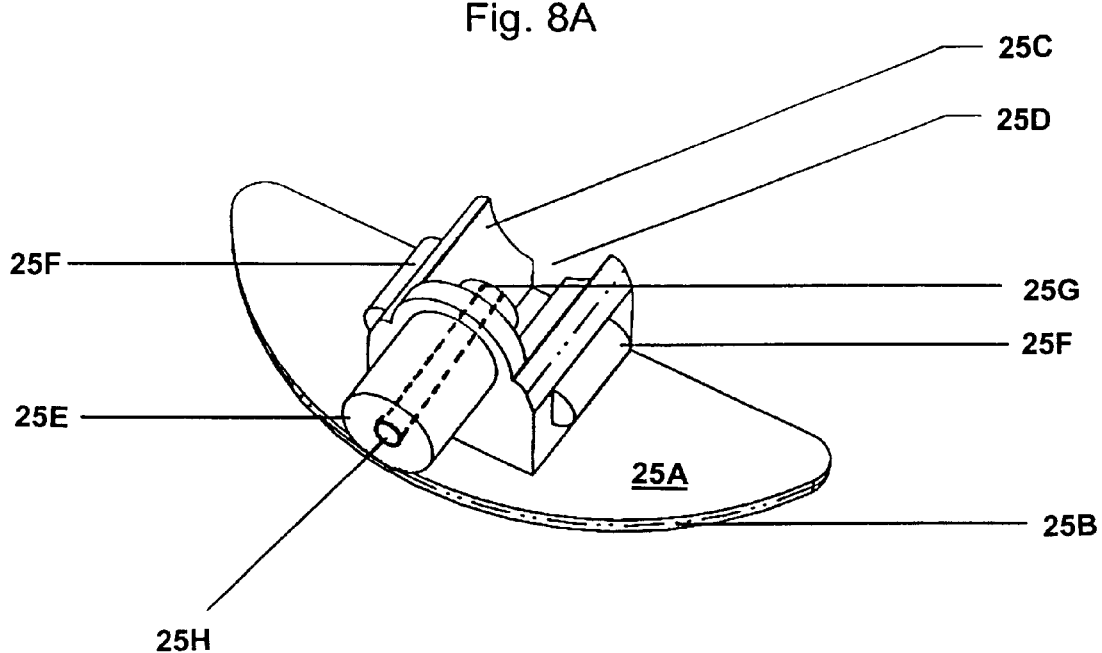
FIGS. 8A and 8B illustrate various views of a plug of a first embodiment of Applicant's present invention.
Figure 8B:
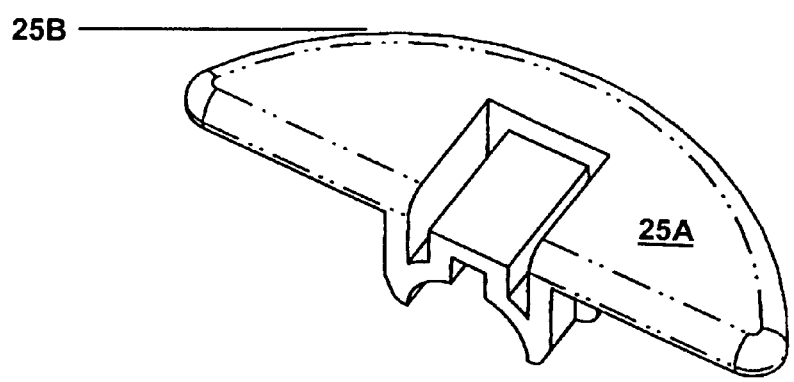

Turning now to FIGS. 8A and 8B details about Applicant's plug (25) may be appreciated. As set forth, the functions of plug (25) are several. The first is to provide a means to effectively guide the handle (30) and needle (32) through the two septums and into the cannula (14C) when Applicant's fluid injection assembly (10) is first engaged in the body of the patient, thereafter which the handle (30) is removed from the remainder of the assembly and discarded. The remainder of the assembly is adhesively attached to the patient's body. A second function of the plug (25) is to provide a means to seal off the removed end of the engagement arm (12C) when the fluid connector (24) is removed therefrom. It may be appreciated that plug (25) may fit snugly against the first septum (18) when the fluid connector is removed therefrom to keep dust and air from reaching that surface.

Bearing these two functions in mind, we turn to the structural details of the plug (25) more specifically with reference to FIGS. 8A and B. Here it is seen that plug (25) includes a cover portion (25A) defined by a cover perimeter (25B), the cover being semi-circular in shape, the shape of the plug (25) being substantially identical to the fluid connector cover (24A), both of these covers being dimensioned to fit within gap portion (12M) of upper lip (12L) of main body assembly (see FIG. 4E). That is, when either the fluid connector or plug (25) are connected to engagement arm (12C) of ball joint (16) and ball joint (16) is in a folded or down position as is set forth in FIG. 1H, then either of the covers will fit snugly within gap portion (12M) of main assembly body (12) such that perimeter (24B) or 25B, as the case may be, will be flush with upper lip (12L) of main assembly body (12).

Plug (25) also includes plug gap portion (25E) and needle guide portion (25G). The plug gap portion (25E) will insert snugly within first end (16F) of central bore (16E) (see FIG. 5C). Plug gap portion (25E) will fit snugly within handle (30) as seen in FIG. 1A. Needle guide portion (25G) of plug (25) will fit snugly within first end (16F) as in FIG. 1A.

Figure 9A:
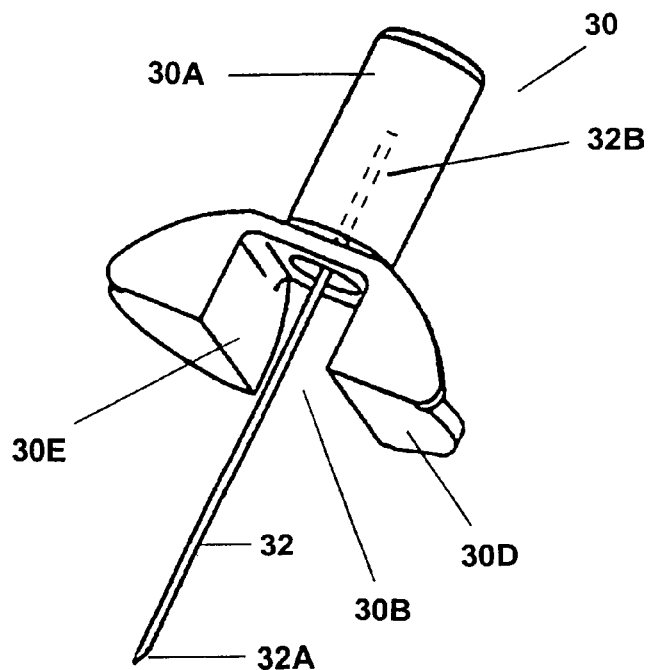
FIGS. 9A and 9B illustrate various views of a handle of a first embodiment of Applicant's present invention.
Figure 9B:
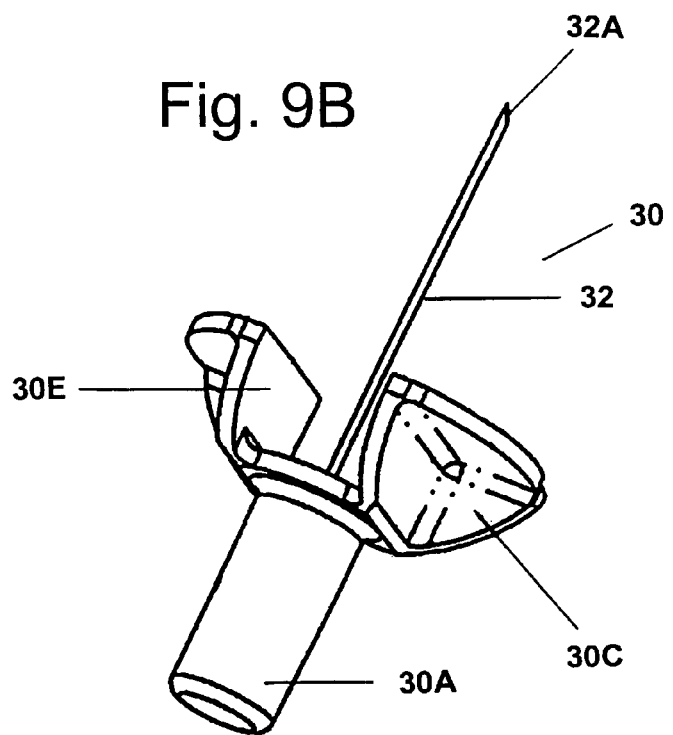

Handle (30) is illustrated in FIGS. 9A and 9B. A function of handle (30) is set forth earlier, that is, to provide a means through use of needle (32) having pointed end (32A) for inserting the cannula 14C under the skin of the patient prior to commencement of delivery of the fluid there into. Thus, handle (30) is seen to engage a long, sharp needle (32)

having a pointed removed end (32A) and a near end (32B) where it joins the rest of the handle. Handle (30) includes a cylindrical elongated grasping portion (30A) and walls defining a guide cutout (30B). The handle also includes vertical walls (30C) and, perpendicular thereto, a base (30D). Adjacent and removed from the grasping portion are a pair of parallel side walls (30E). Side walls (30E) engage the plug (25) as set forth in FIG. 1A and 1B to seat needle (32) in plug opening (25H). Thus, the purpose of the handle (30) is to cooperate with the plug (25) to maintain the needle (32) with elongated opening (25H) which is itself aligned with the longitudinal axis of cannula (14C). When handle (30) is inserted through the two septums its central longitudinal axis will be coincident with the longitudinal axis of cannula (14C). Further, the depth to which the handle (30) is inserted is sufficient so the needle pointed end (32A) projects just moved end of cannula (14C) as seen in FIG. 1B. The cannula is perpendicular to the lower surface of the assembly body. This makes for efficient emplacement of the assembly body onto the patient. Note that the delivery tube comes into the assembly body perpendicular to the cannula and almost flush with the skin. This device is unique in providing a cannula projecting perpendicular into the surface of the skin while providing delivery tube that joins the assembly body perpendicular to the cannula and almost flush with the skin. This helps provides a "low profile" and a "snag free" assembly.

Applicant also notes that any or all parts of Applicants invention may be made from antibacterial materials known in the trade. Further, Applicant has provided in a fluid injection assembly (10) a ball joint (16) that is rotatable between a position perpendicular and position parallel to and coincident with the cannula (14C). Applicant provides for, in an alternate prefer-red embodiment, snaps, detents or other means to releaseably retain the ball joint (16) in the perpendicular position, the parallel position and also a position half-way between the two, or at 45 degrees with respect to the perpendicular. This provides an additional position should the patient want to use the assembly without the ball joint (16) being either perpendicular or parallel.

FIGS. 10A through 10J, 11A through 11F, 12A through 12G, 13A through 13H, 14A through 14C, 15A through 15G, 16A through 16G, and 17A through 17F, disclose details of a preferred embodiment of Applicant's fluid injection assembly (110). This embodiment has some features different than from the embodiment presented earlier. It has no main body, rather uses a base and a left cover and a right cover as explained in more detail below. Further, it has a positive locking is mechanism that will lock the rotating joint in a down position. These and other features will be explained in more detail below.

Turning now to FIGS. 10A through 10J, it will be noted that FIGS. 10A through 10E illustrate a fluid injection assembly (110) with a handle (130), a two piece cover, here a right cover (122') and a left cover (122"). The two covers engage abase (114) which has a flat bottom surface (114B), the bottom surface (114B) of which is attachable to the patient's skin. Projecting perpendicular downward from the bottom surface (114B) of base (114) is a cannula (114C). As will be set forth in more detail below, the embodiment illustrated in FIGS. 10A through 17G includes Applicant's novel rotating joint. However, the embodiment illustrated in FIGS. 10A through 17G also includes a number of desirable features including a lock (117) which will lock the rotating joint in a "down" position. This embodiment also eliminates the main assembly body of the previous embodiment, the functions of which are taken care of primarily by base (114) and covers (right and left) (122') and (122").

Figure 10A:
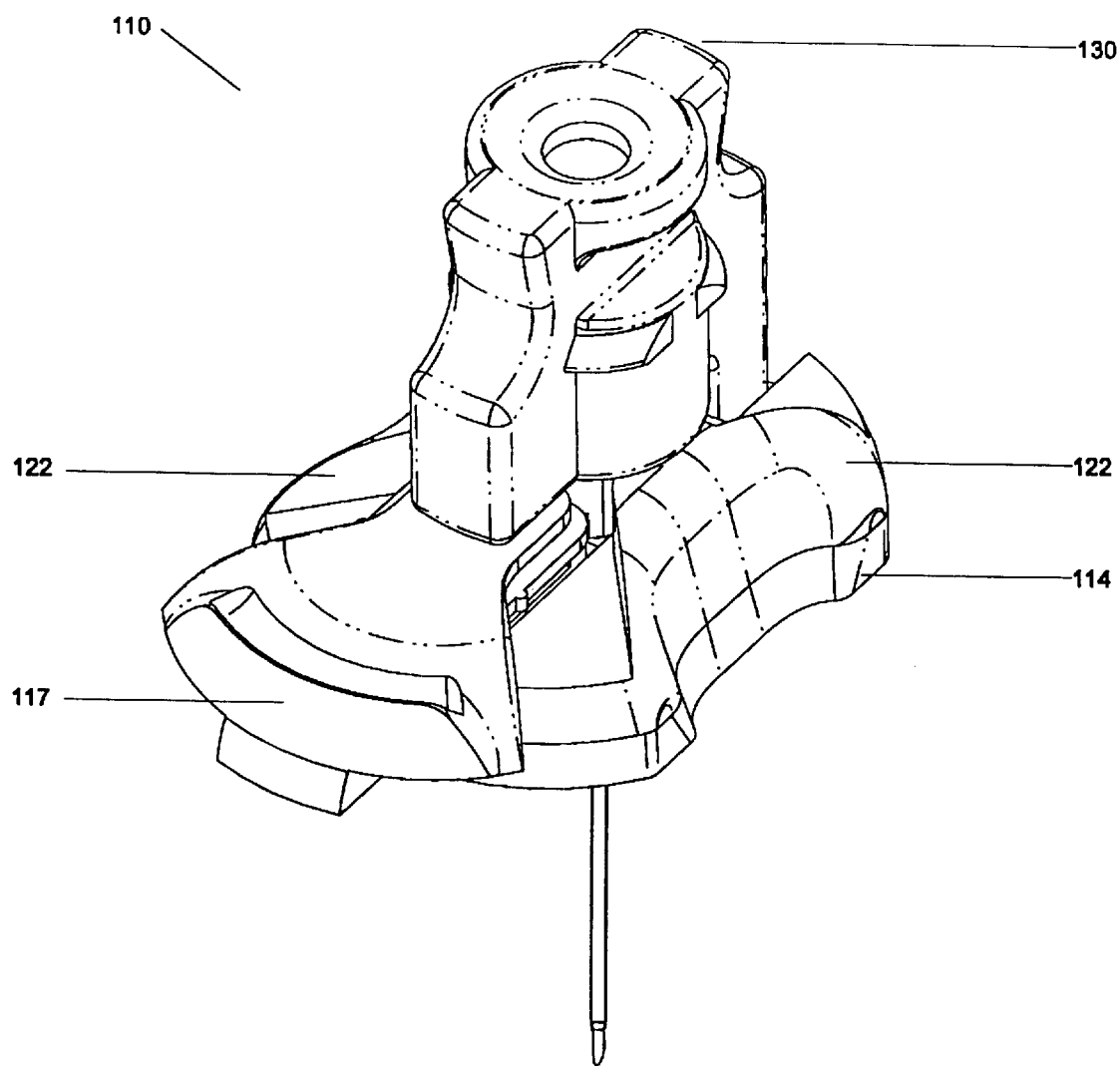
FIGS. 10A through 10E illustrate a second embodiment of Applicant's present invention in a position and in a condition in which it may be placed on the patient, that is, with handle (130) having a needle (132) therein.
Figure 10B:
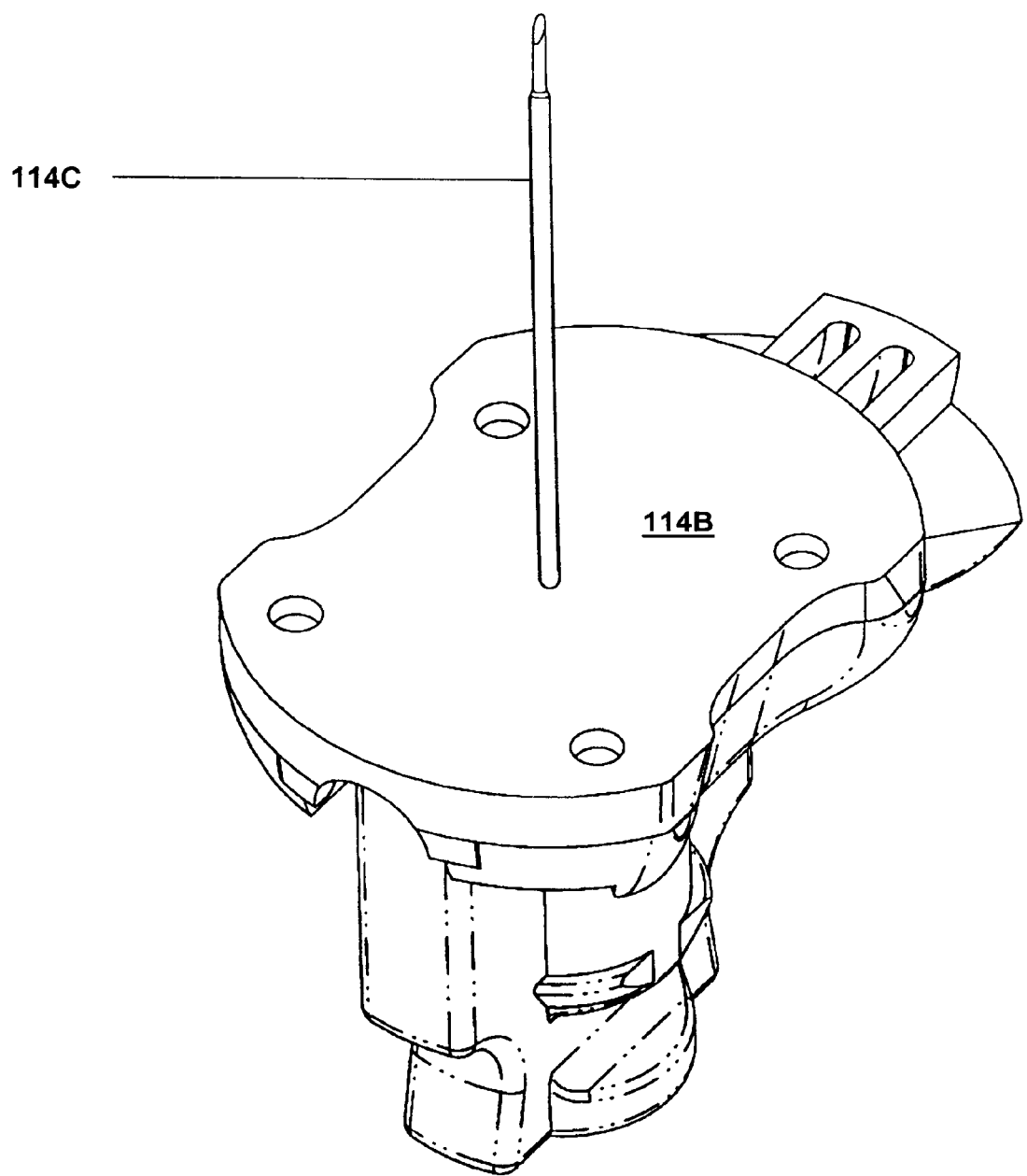
Figure 10C:
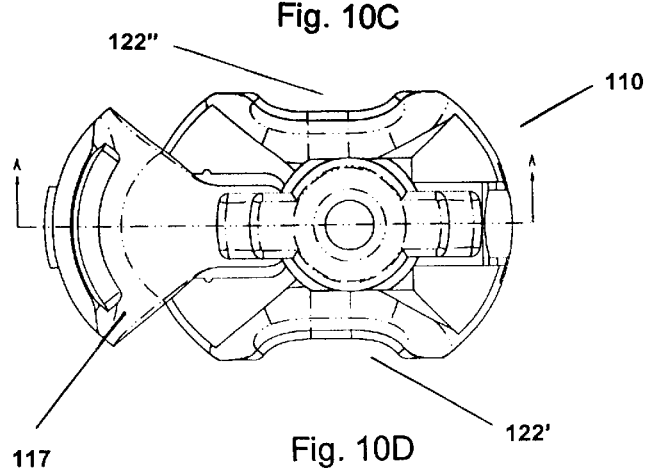
Figure 10D:
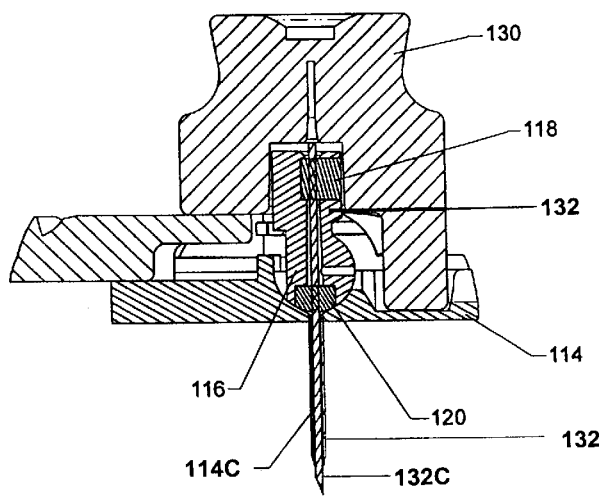
Figure 10E:
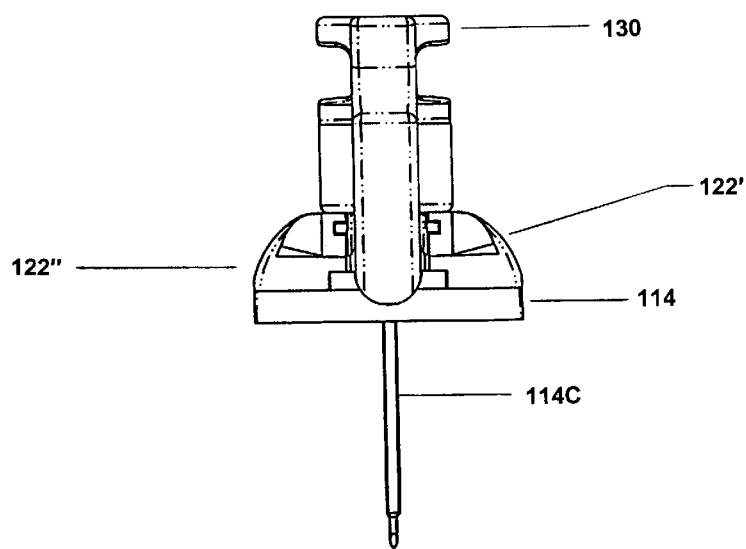
Figure 10F:
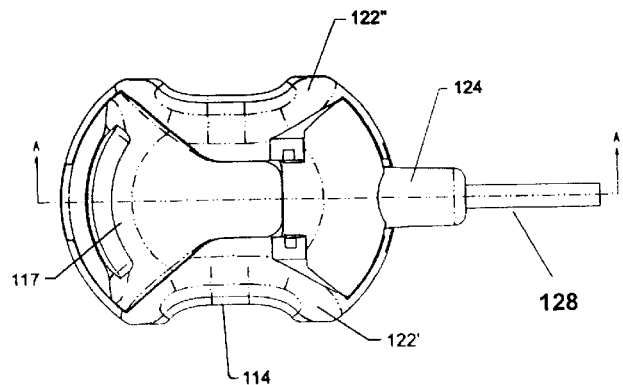
FIGS. 10F through 10J illustrate various views of a second embodiment of Applicant's present invention with a fluid connector attached thereto in a "down" or use position, that is, when transferring fluid from a remote vessel into the body of a patient.
Figure 10G:
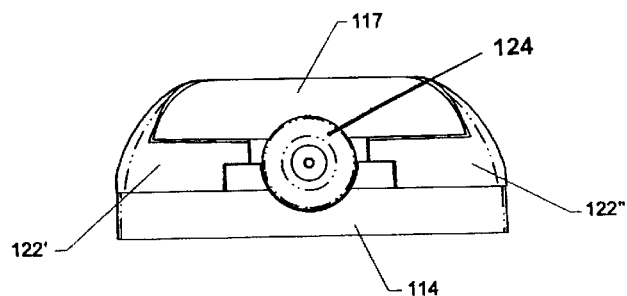

FIGS. 10A and 10D illustrate fluid injection assembly (110) with handle (130) engaged therewith which handle (130) has a needle that extends through cannula (114C). In FIGS. 10A and 10D, lock (117) is seen to be in an "out" or disengaged position. In the configuration illustrated in FIGS. 10A–10E, fluid injection assembly (110) is ready to be placed on the patient's body with lower surface (114B) of base (114) typically having an adhesive thereon which will help hold the unit to the skin of a patient. Upon placement of fluid injection assembly (110) on the patient, handle (130) may be withdrawn and discarded and pivoting joint (116) (see FIG. 10H or 10I) may be rotated out of the up position and fluid connector (124) may be engaged therewith for delivery of a fluid to the patient. Note FIGS. 10F–10J all illustrate fluid injection assembly (110) with the fluid connector (124) engaged therewith.

Figure 10H:
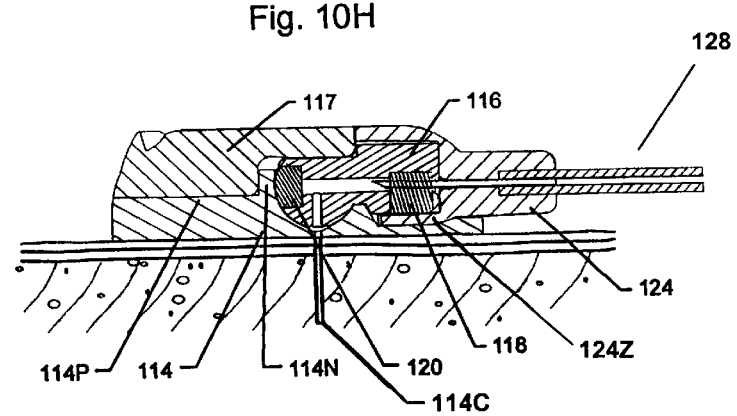

Turning now to FIGS. 11A through 11F, details of Applicant's base (114) may be appreciated. Base (114) is seen to have perimeter walls (114A), bottom surface (114B), top surface (114G), ball joint support arm recesses (114K), pivoting joint body recess (114J), engagement arm recess (114L), apertures (114M), and pivoting joint seat (114I). The function of the base (114) and these features are several. First, base (114) provides support for rotating or pivoting joint (116). More specifically, pivoting joint seat (114I) and pivoting body recess (114J) provides support for rotating joint (116) whatever position the rotating joint (116) happens to be in. Furthermore, walls (114A) of base (114) are configured to at least partially except rotating joint (116) when it is in a down position, namely, engagement arm recess (114L) and bay (114F). Further, base (114) contains apertures (114M) which will accept left and right covers 112" and 112'. To this extent, base (114) is functionally similar to base (114) of the earlier embodiment illustrated. However, there are additional features to base (114) illustrated in FIGS. 10A through 17G that may be appreciated with reference to the illustrated figures. For example, base (114) provides a lock stop (114N). Stop (114N) acts as a stop against which lock (117) may rest as seen in FIG. 10H. Base (114) is also seen to have walls defining left channel (1140") which engage the lock (117) to the base (114) (See FIG. 10I). As the lock (117) slides in channel (1140") it will be prevented from backing out from the base by walls (114Q), partially blocking these channels. Further, base (114) includes land (114P), also for accepting and guiding lock (117) between an in and an out position as set forth in more detail below (See FIG. 10H).

FIGS. 12A through 12G illustrate details of Applicant's rotating joint (116). While in the previous embodiment this functionally similar structure was sometimes referred to as a "ball joint" it is being called a "pivoting" or "rotating" joint (116) here, in an effort to point out that while a "ball" shape, may, in part, provide for pivoting, in fact, the particular geometry of the structure is not crucial to its rotating nature. That is, rotating joint (116) is, similar to the ball joint, a rotating element which has channels within in which will allow the insertion of a handle through the joint when the joint is in a first position and, upon rotation will allow connection between a fluid carrying connector and the cannula when it is in a second position, typically rotated any number of degrees, for example, 90° from the first position. Ball joint or pivoting joint (116) is seen to have, typically, at least a partially spherical portion (116A) and a pair of support arms (116B). The support arms (116B) and at least part of portion (116A) will rest in portions of base (114) as seen with reference to FIGS. 10H and 11A. Engagement arm (116C) will be seen to have central bore (116E) and central portion (116H) of central bore (116E) aligned coincident with the longitudinal access of the engagement arm (116C). Moreover, the axis of support arms (116B) is perpendicular to the axis of engagement arm (116C). Thus, the general design of any of the pivoting members of Applicant's invention includes two bores through the body of a pivoting member which are perpendicular to one another and to the axis of rotation, the two bores or channels for carrying fluid from a fluid connector to the cannula. Perpendicular to one of those two bore will be a central bore to carry the needle which engages the handle, for placement of the device on the skin of the patient.

Ball joint or pivoting joint (116) is also seen to have guide member (116D) which assists in engaging and guiding fluid connector (124) onto pivoting joint (116). Pivoting joint (116) and ball joint (16) both contain a similar arrangement of channels or bores throughout the body thereof. The purpose these is twofold. First, a bore must be provided such that when the joint is in an up or vertical position a handle is engaged therewith, the handle having an insertion needle projecting downward through the cannula. The second function of the bores or channels in the body of the pivoting joint is for carrying fluid from the fluid connector to the cannula. Applicants have found a novel arrangement of bores in which there is a central bore and, perpendicular thereto, a feed bore. The central bore including central portion (116H) will carry the needle of the handle when the device is placed on the patient. At least part of the central bore of Applicant's novel pivoting member will also provide for carrying fluid to the patient. However, Applicant also provides, perpendicular to the central bore, a feed channel bore (116I) which completes the necessary passageway to carry fluid from the fluid connector to the cannula (and into the patient) when the pivoting member or ball joint is in a down position. It is noted here that the pivoting or ball joint typically rotates about an axis perpendicular, and going through, the junction of the central bore and the feed channel bore.

Note with reference to FIG. 12 G, that pivoting joint (116) has a first cut out (116F) and a second cut out (116G) the first cut out (116F) being at the first end and the second cut out (116G) being at the second end, the two cut outs dimensioned for receipt of septums thereinto (see FIG. 10H). First cut out (116F) brings the septum in from the side of the engagement arm instead of from the front engagement arm as set forth in the earlier embodiment (compare FIGS. 1A and 10H). Ball joint or pivoting joint (116) also has an aperture (116J) at the end of feed channel bore (116I) for carrying fluid into the patient when the pivoting joint (116) is in a down position (See FIG. 12F). Note with reference to FIG. 12A that support arms (116B) have a right locking ridge (116K') and a left locking ridge (116K") for engagement with cut outs in the left cover (122") (left locking ridge (116K")) and right cover (112') (right locking ridge (116K')). Details of how the locking ridges engage the covers will be set forth in more detail below and with reference to FIG. 10I.

Figure 13A:
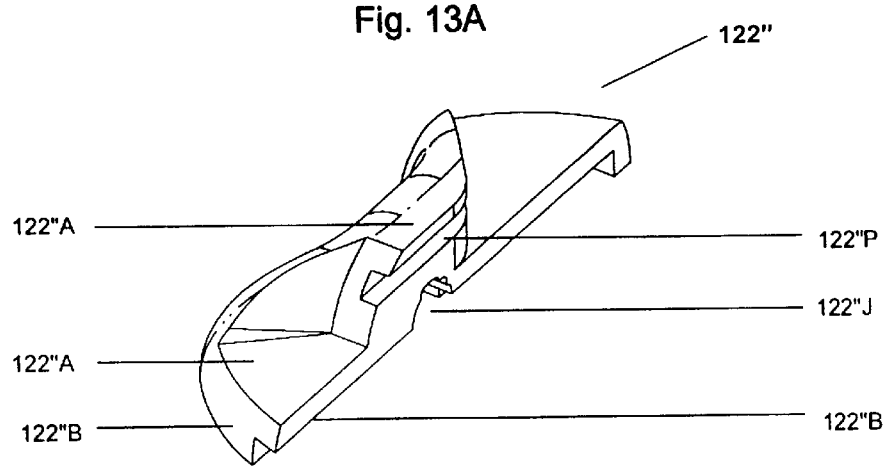
FIGS. 13A through 13H illustrate a left side cover for use with a second embodiment of Applicant's present invention.
Figure 13B:
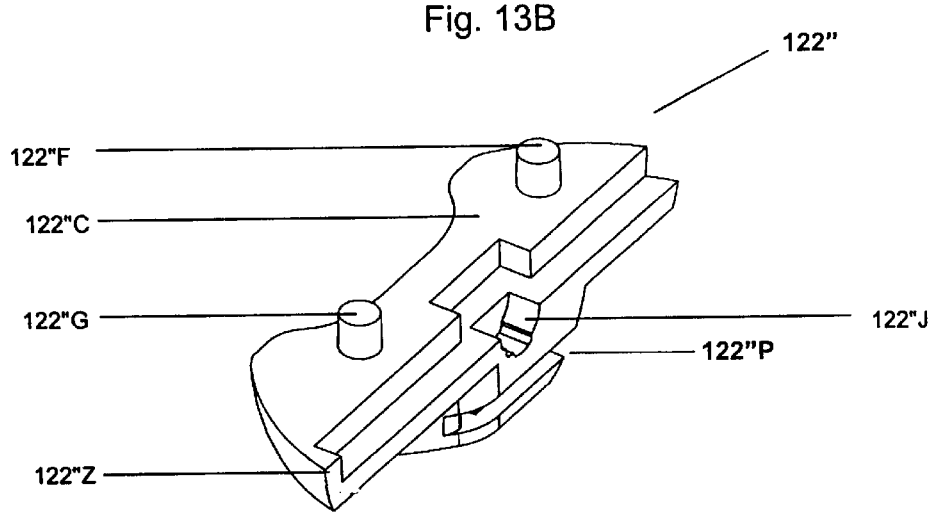
Figure 13C:
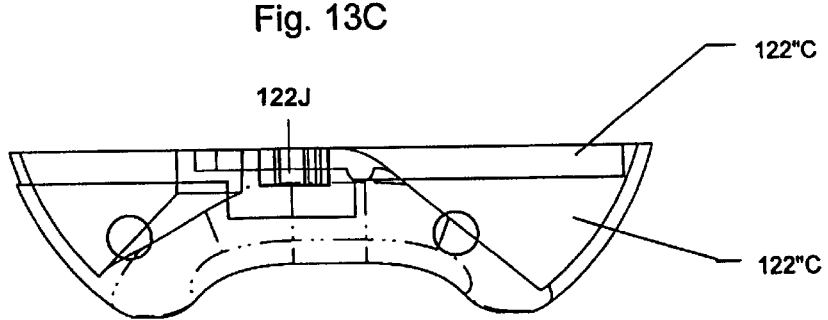
Figure 13D:
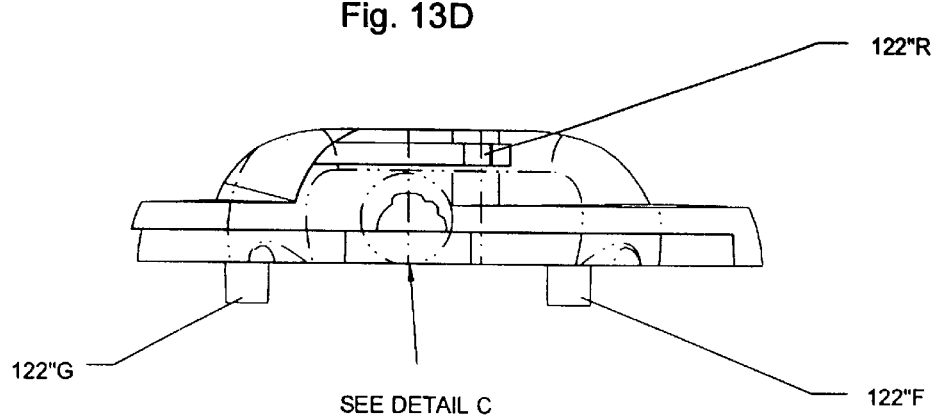
Figure 13E:
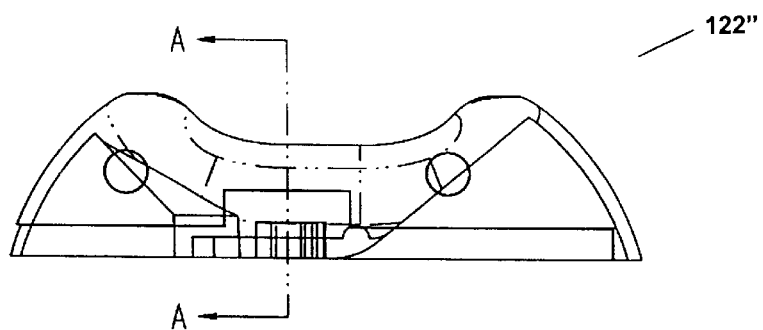
Figure 13F:
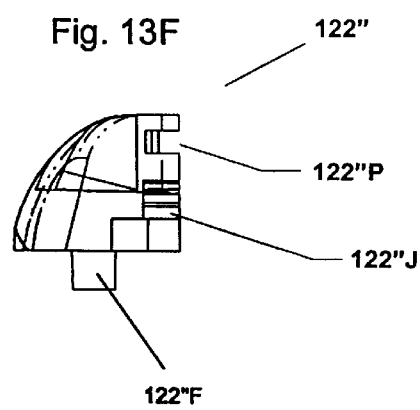
Figure 13G:
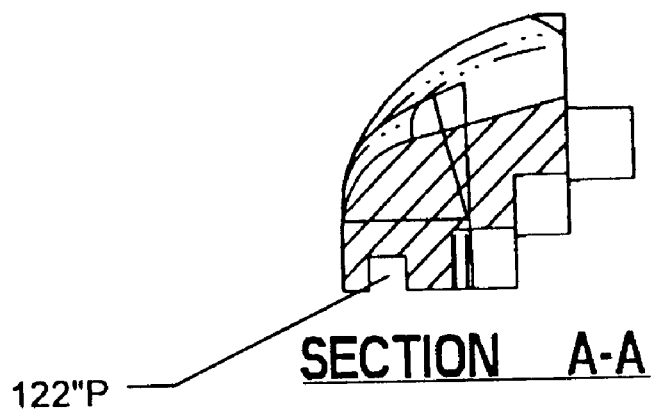
Figure 13H:
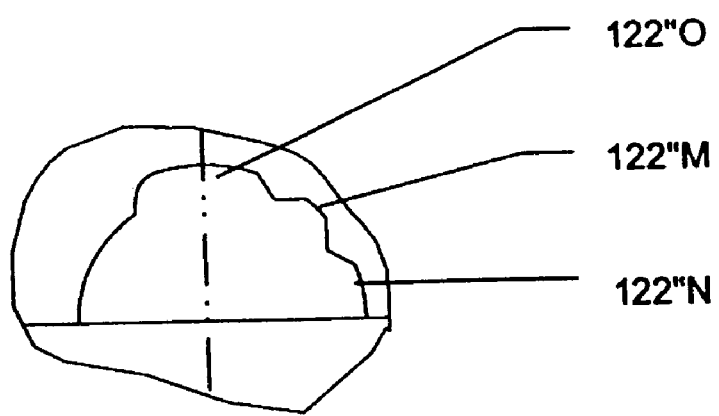
Figure 14A:
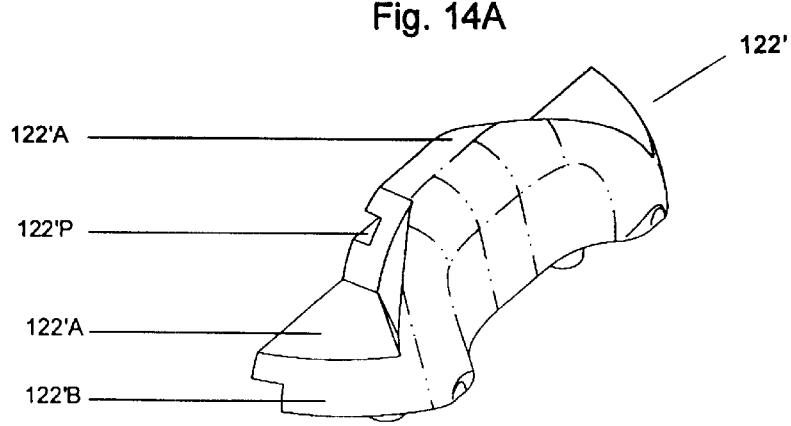
FIGS. 14A through 14C illustrate a right side cover for use with a second embodiment of Applicant's present invention.
Figure 14B:
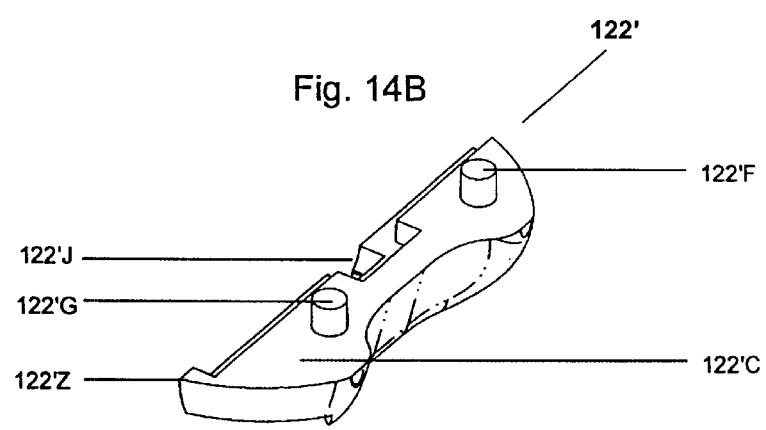
Figure 14C:
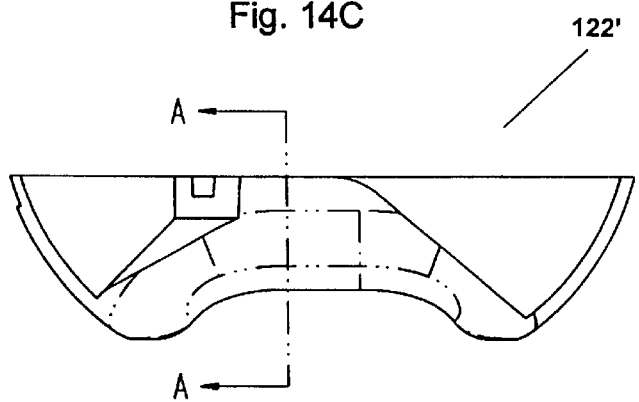
Figure 15A:
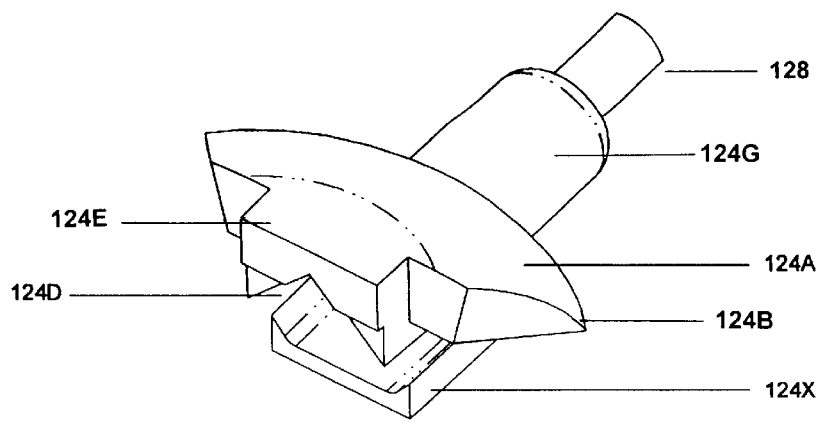
FIGS. 15A through 15G illustrate a fluid connector for use in a second embodiment of Applicant's present invention.
Figure 15B:
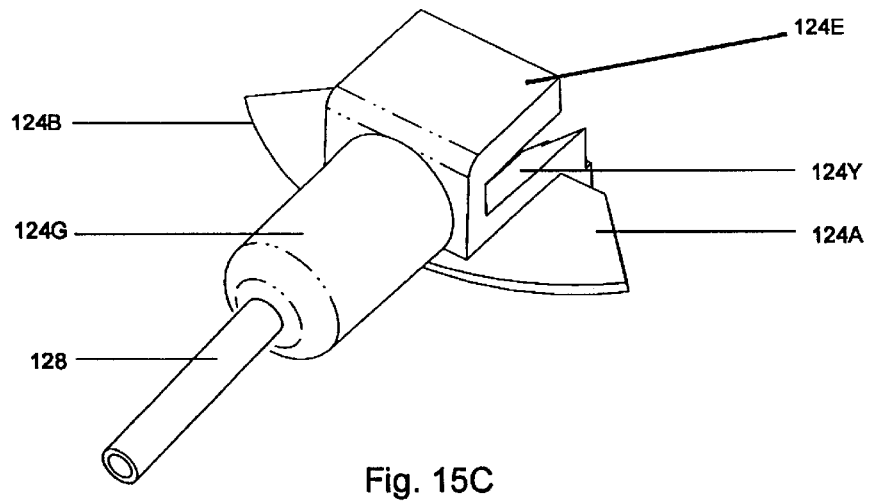
Figure 15C:
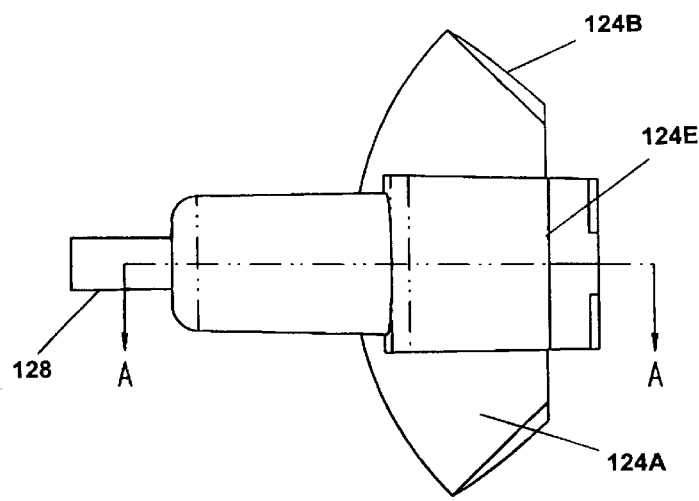
Figure 15D:
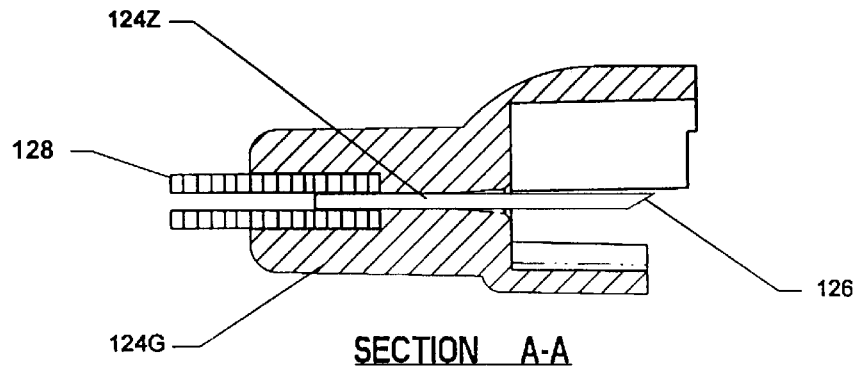
Figure 15E:
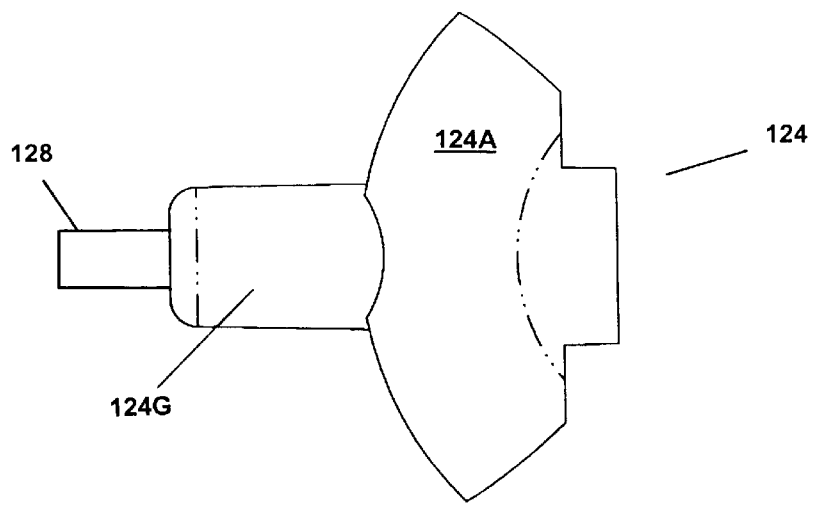
Figure 15F:
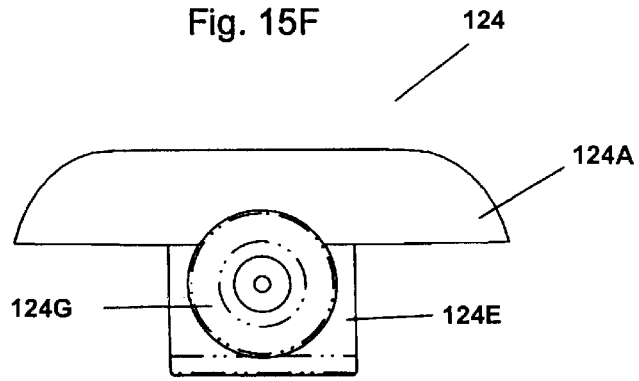
Figure 15G:
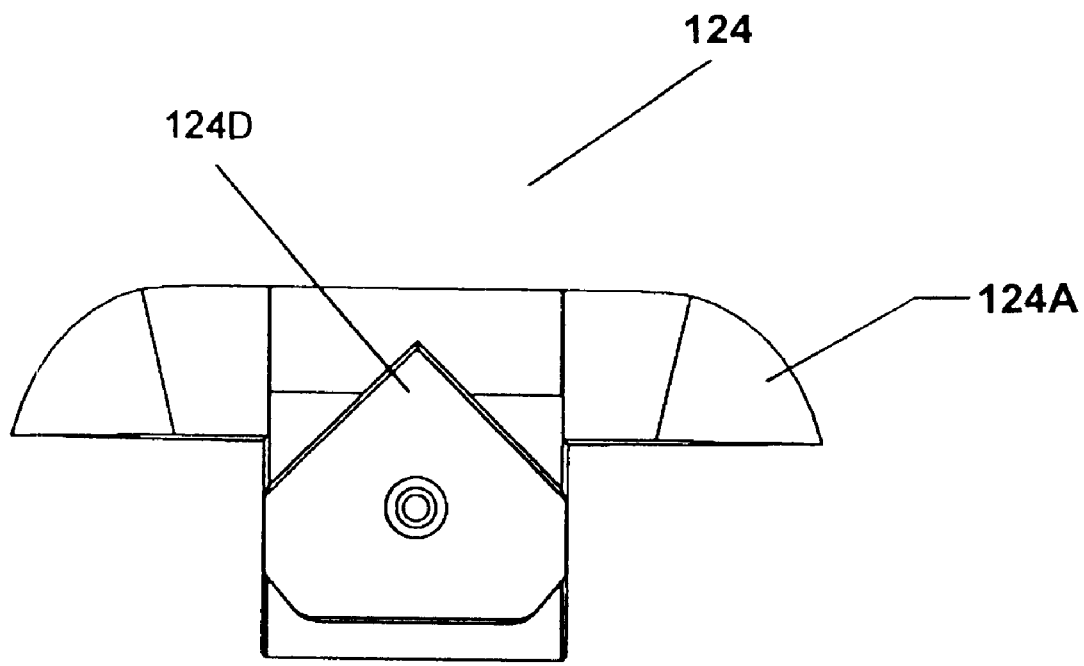
Figure 16A:
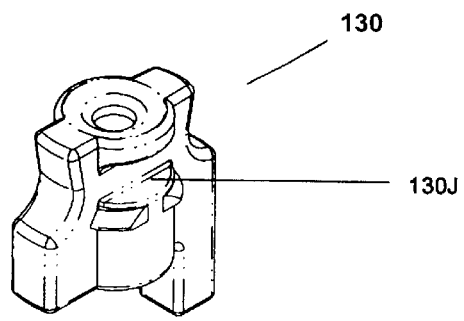
FIGS. 16A through 16G illustrate a handle for use with a second embodiment of Applicant's present invention.
Figure 16B:
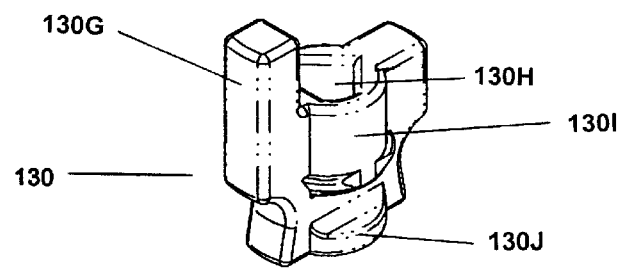
Figure 16C:
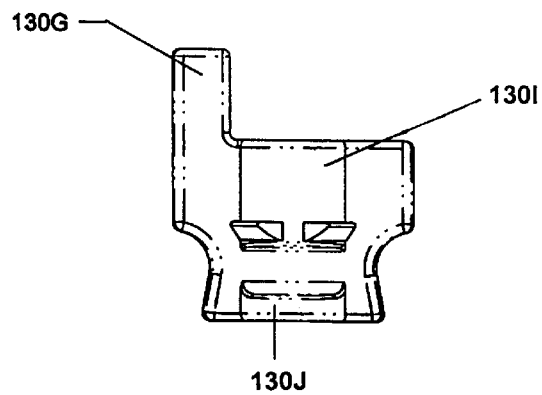
Figure 16D:
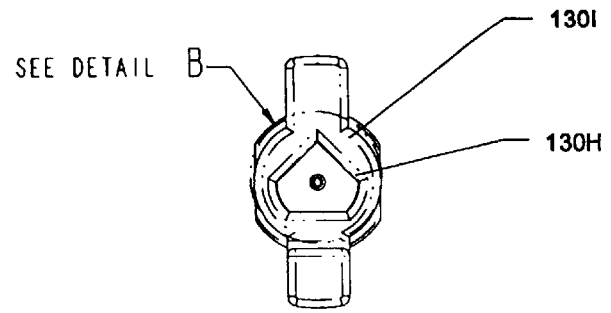
Figure 16E:
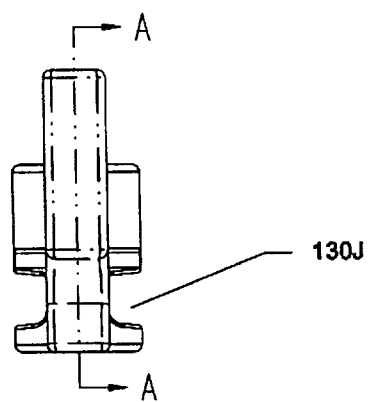
Figure 16F:
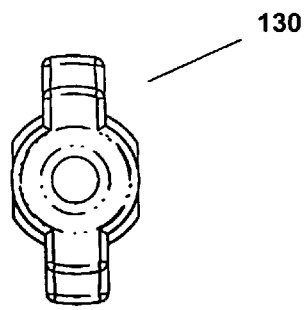
Figure 16G:
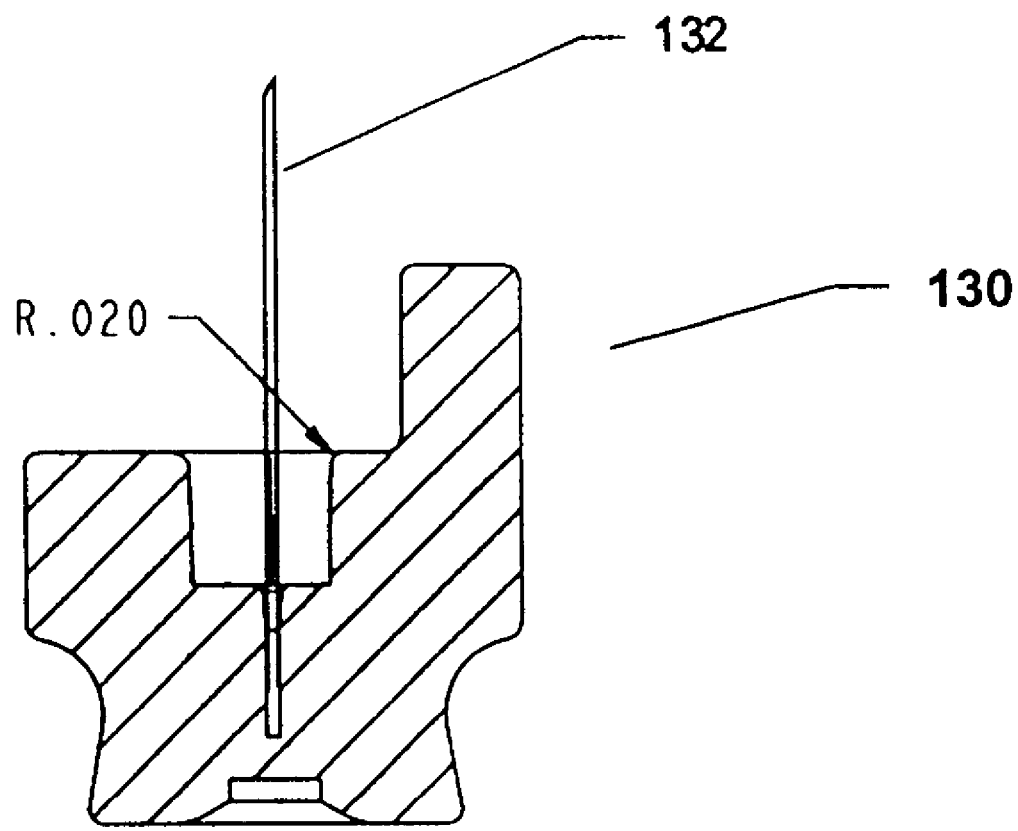
Figure 17A:
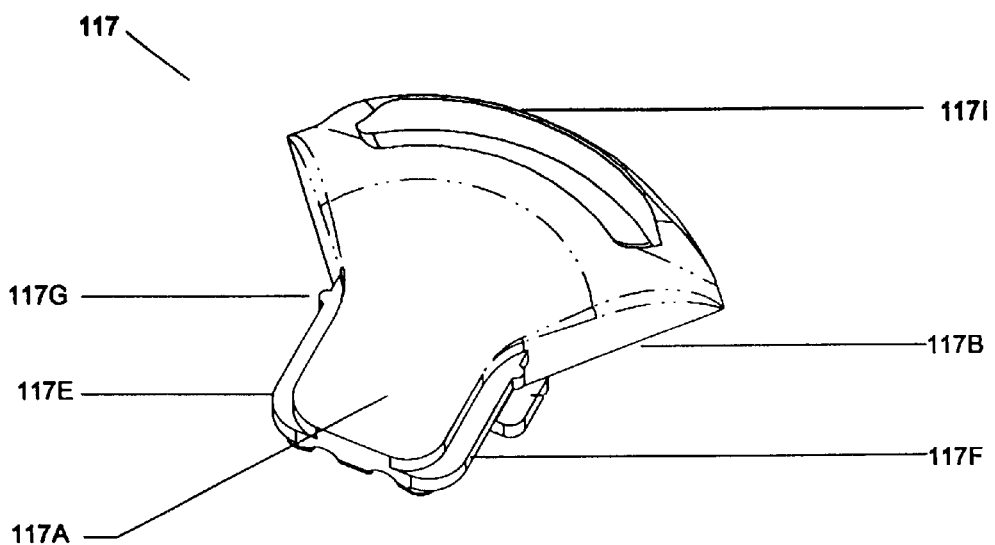
FIGS. 17A through 17F illustrate a lock for use with a second embodiment of Applicant's present invention.
Figure 17B:
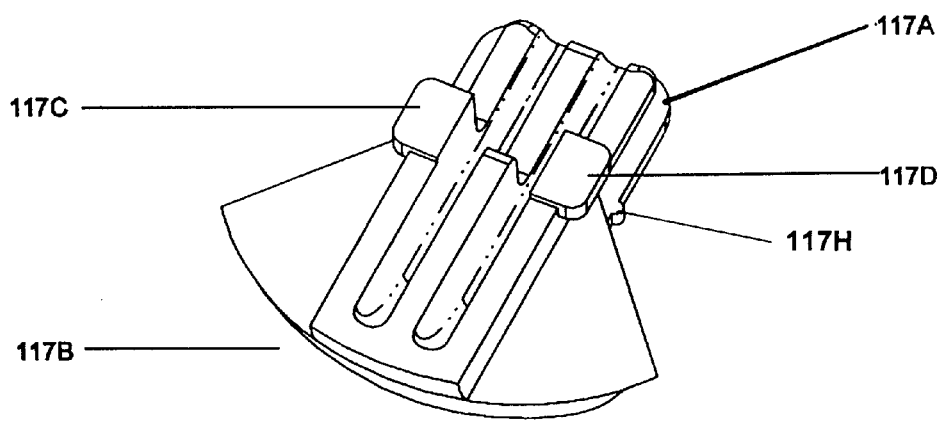
Figure 17C:
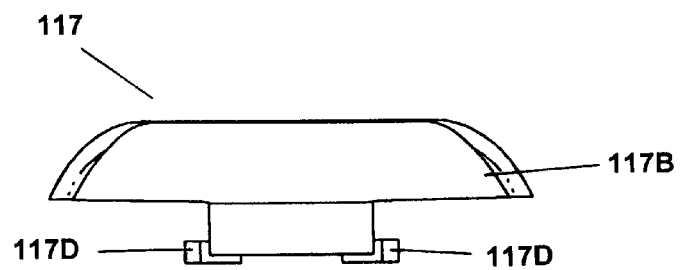
Figure 17D:
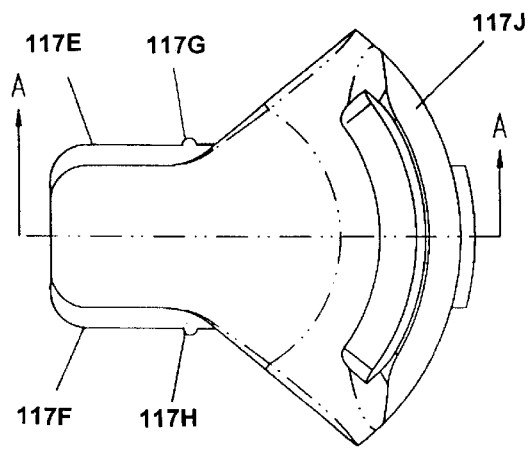
Figure 17E:
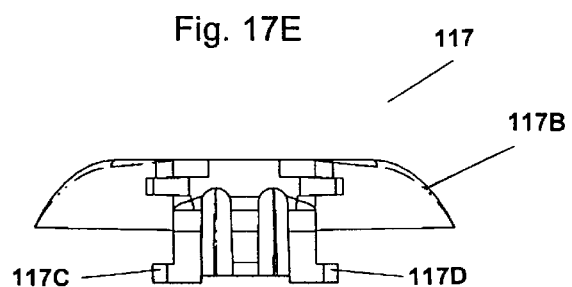
Figure 17F:
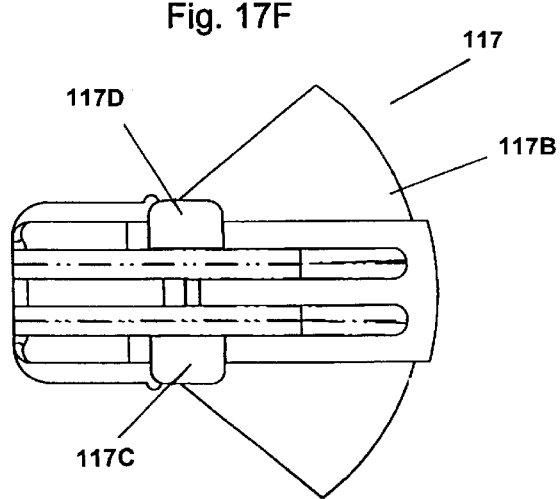

Turning now to FIGS. 13A through 13H, which illustrate left cover (122") and FIGS. 14A through 14C, which illustrate right cover (122'). Please note that the two covers are symmetrical about longitudinal axes and therefore the discussion with respect to left cover (122") should be used to understand right cover (122'). FIGS. 13A and 13B illustrate isometric views of left cover (122"). It is seen to include a top surface (122"A) and perimeter walls (122"B). The cover also includes a lower surface (122"C) and a pair of legs (122"F) and (122"G). Each cover also includes a support arm cut out, here in FIGS. 13B (122"J). As seen with referenced FIG. 13H, support arm cut outs include three bays: (122"N), (122"M) and (122"O). The function of the three bays is to engage the locking ridge, (116"K) of pivoting joint (116), so as to maintain or assist in maintaining ball joint in the down position (bay (122"O) or a 45° position (bay (122"M) or in a vertical or up position (bay (122"N), the up position for engagement with the handle and the down or 45° position for connecting to the fluid connector. Support ridges (122") between the bays are dimensioned to provide some interference with the locking ridges while still allowing movement of the ball joint over the ridges that separate the bays (see FIG. 10I). Cover left (122") also includes a slot (122"P) for slidably engaging the wings (117E and 117F) of lock (117) (see FIG. 17A and FIG. 10I). Locate cove (122"R) in slot (122"P). This will engage a boss (See 117G and 117H) on the wings when the lock 117 is engaged. It is further seen that part of perimeter walls (122"B) define shoulder (122"Q) such that when the cover is engaged with the base, the shoulder along with the base will provide a channel in which the tabs (117C and 117E) of the lock (117) will ride. Note that left cover (122") is connected to the left side of the base by the insertion of legs (122"F and 122"G) through apertures of the base (114) such that there is a flush engagement with lower surface (122"C) with the base. Glue or other appropriate adhesives may be used for affixing the covers to the base.

FIGS. 14A to 14C illustrate details of right cover (122'). Right cover (122') includes top surface (122'A), perimeter walls (122'B), lower surface (122° C), legs (122°F), and (122'G), support arm cut outs (122'J) as well as bays, slot, shoulder portion, and the remaining elements of the left cover. It is noted that right cover and left cover will, when affixed to the base provide support arm cut outs to support the support arms of the pivoting joint (116) as well as provide a pair of slots for engaging the wings of the lock and also will prepare a channel in which tabs of the lock can ride.

Turning now to connector (124), and FIGS. 15A–15G it is seen that connector (124) is designed to carry fluid into pivoting joint via a connection of a needle piercing the first septum (118) (see FIG. 10H). Fluid connector (124) includes a cover (124A) having a cover perimeter (124B). The fluid connector also has a body portion (124E) and extending from the body portion is a feed tube engagement portion (124G) for engagement with a flexible feed tube (128). The feed tube will carry fluid and joins the needle (126) in feed tube engagement portion (124G) (see FIG. 15D). It is seen that the needle (126) is held in body channel (124Z) such that the feel tube engages the needle (126). Body portion (124E) contains slots (124Y) which slots will engage the outer edges of engagement arms (116C). Note that "V" shaped pivoting joint guide notch cut out (124D) will guide "V" shaped fluid connector onto the "V" shaped engagement arm (116) of the pivoting joint while aligning needle (126) with first septum of the pivoting joint and the central bore. Moreover, body (124E) of the fluid connector includes land (124X) that will seat within of the engagement arm recess (114L) of base (114) when the connector is pushed onto the engagement arm and then the engagement arm is rotated to a down position (see FIG. 10H). Fluid connector (124) is typically urged onto the engagement arm when the engagement arm is in a 45° or a vertical (up) position until it is flush and then the joint is rotated to a down or 0° position (see FIG. 10H). This rotation of the coupled fluid connector (124) and ball joint (116) should be done with a lock in an "out" or disengaged position. When the coupled fluid connector joint engagement arm unit is rotated down lock 117 can be slid forward until it is fully engaged against stop (114N) and nose (117A) overlies at least a portion of the rotating joint (116) as set forth in FIG. 10H, 10I and 10J. When the lock (117) is moved forward it will hold down the pivoting joint (116).

FIGS. 16A through 16G illustrate features and construction of Applicant's handle (130). These illustrations may be used in conjunction with FIGS. 10A through 10E to help illustrate the functions of the handle (130). Handle (130) is provided with needle (132). Its function is to engage the remaining elements of fluid injection assembly (110) in such a fashion as to maintain needle (132) within cannula (114C) with enough rigidity to insert the unit on the patient without crumbling the cannula (114C). The handle (130) fits onto the base and covers with the lock in an "out" position as illustrated in FIG. 10A. Handle (130) includes finger cut outs (130J) to help hold the unit when placing it onto the patient. Alignment stub (130G) sits into engagement arm recess (114L) of base (114) (see FIG. 10D). It is also seen how handle (130) has body (130I) with engagement arm recess (130H) which engagement arm recess is shaped to receive the engagement arm of the pivoting joint (116) there into as seen in FIG. 10D. Handle body (130I) also includes engagement arm recess (130H) with needle (132) mounted along a longitude axis of the handle (130).

Figure 10I:
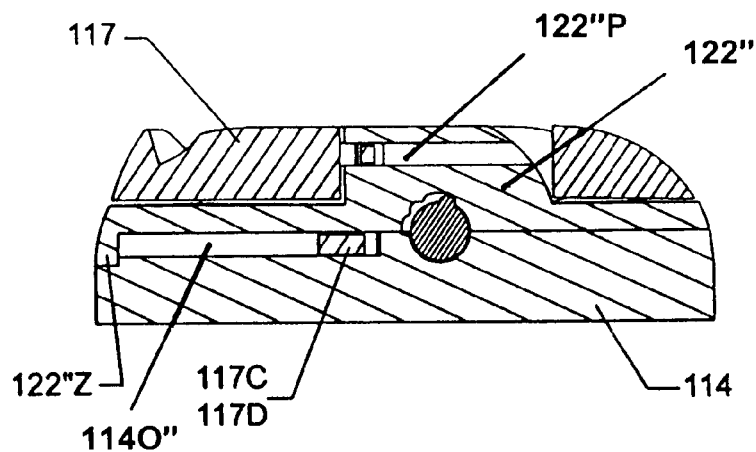
Figure 10J:
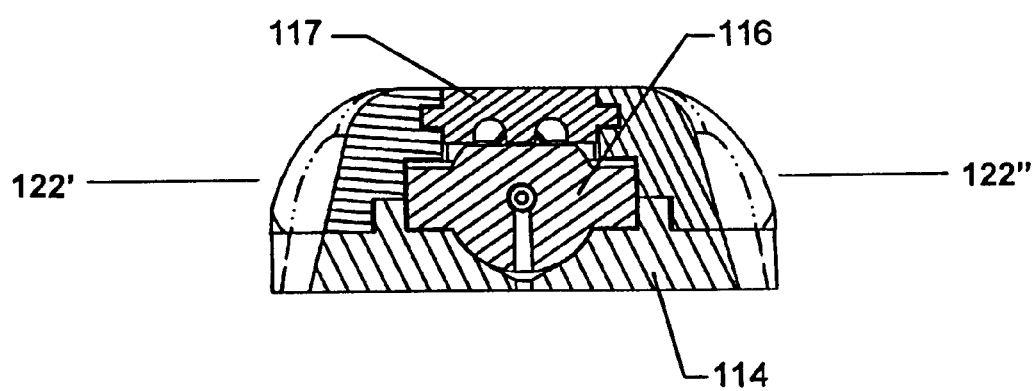
Figure 11A:
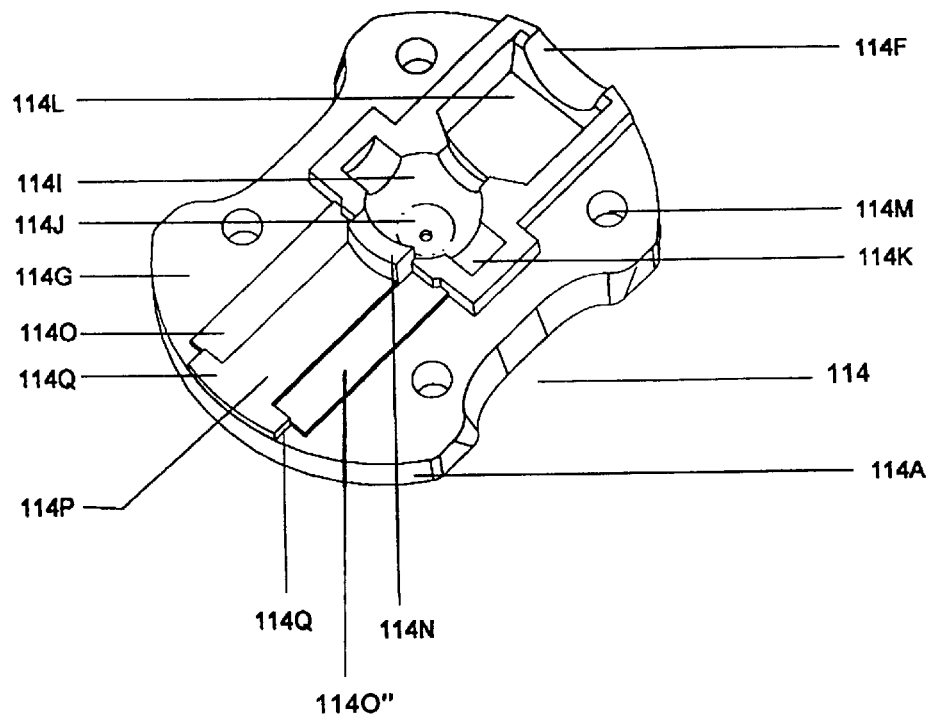
FIGS. 11A through 11F illustrate a base for use with a second embodiment of Applicant's present invention.
Figure 11B:
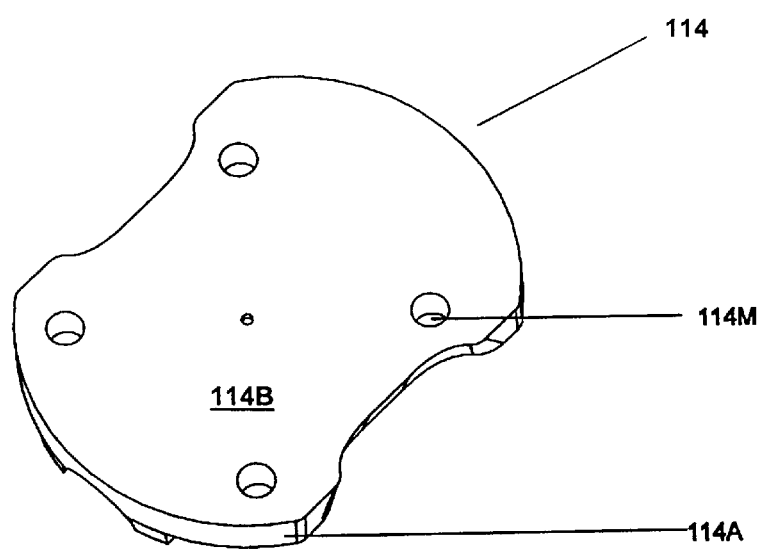
Figure 11C:
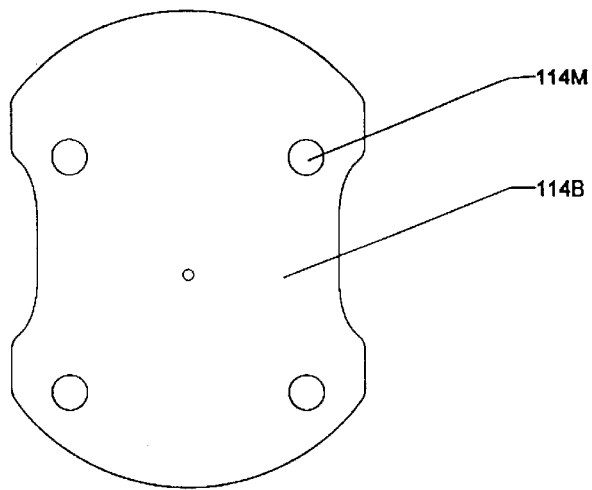
Figure 11D:
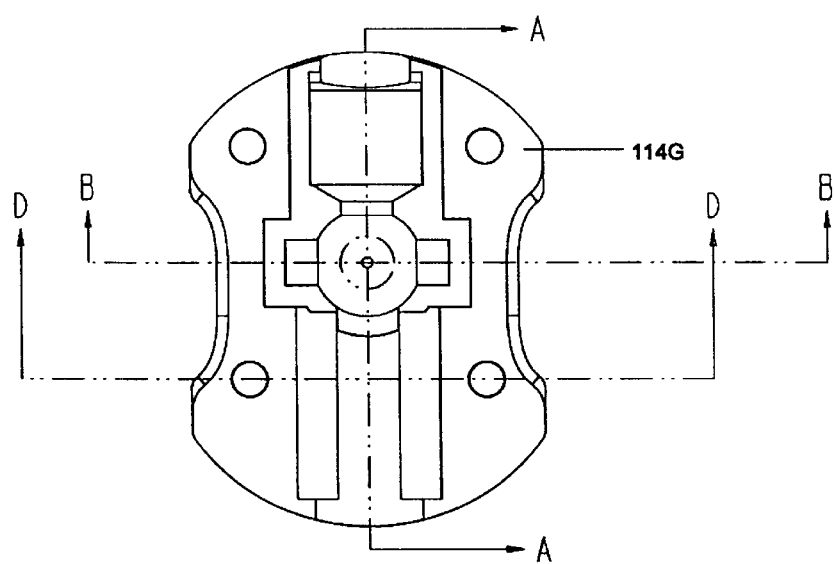
Figure 11E:
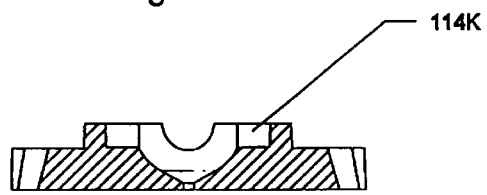
Figure 11F:
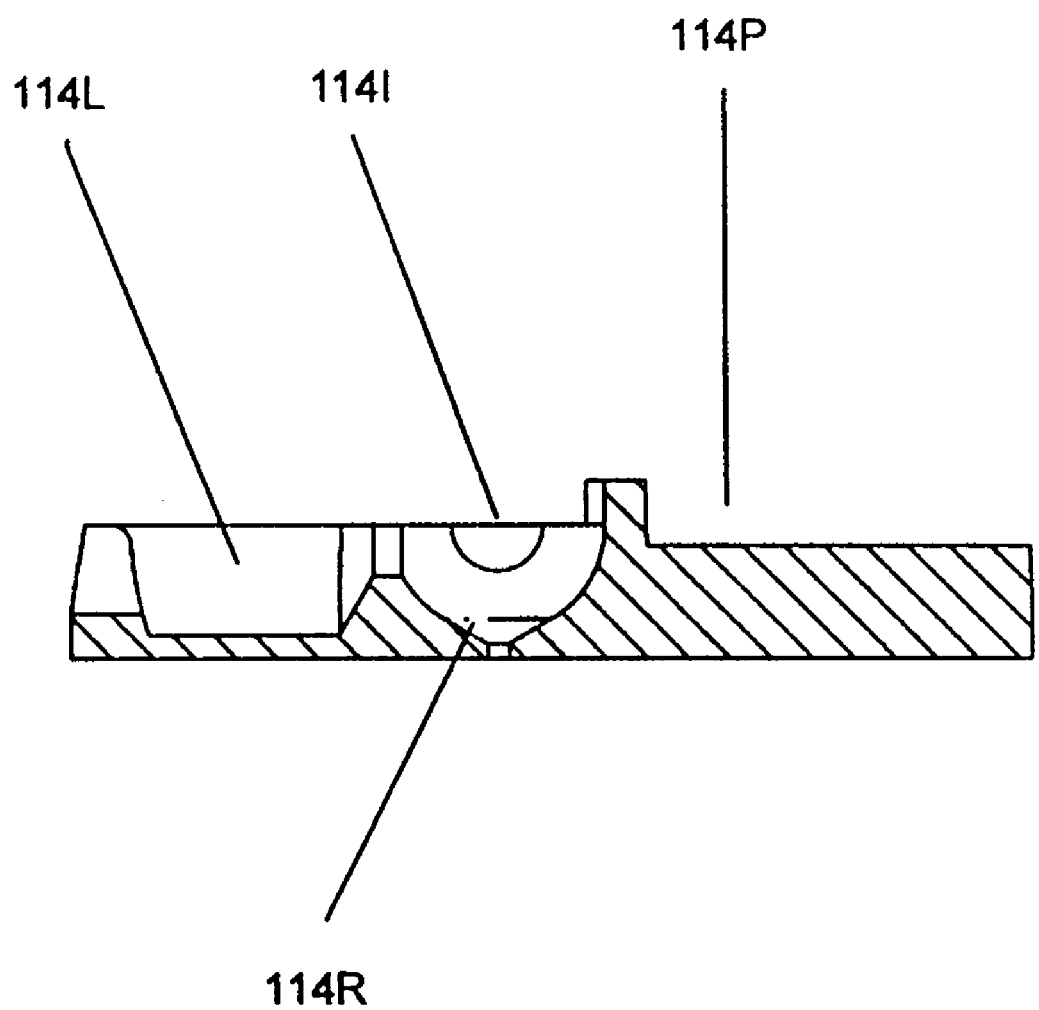
Figure 12A:
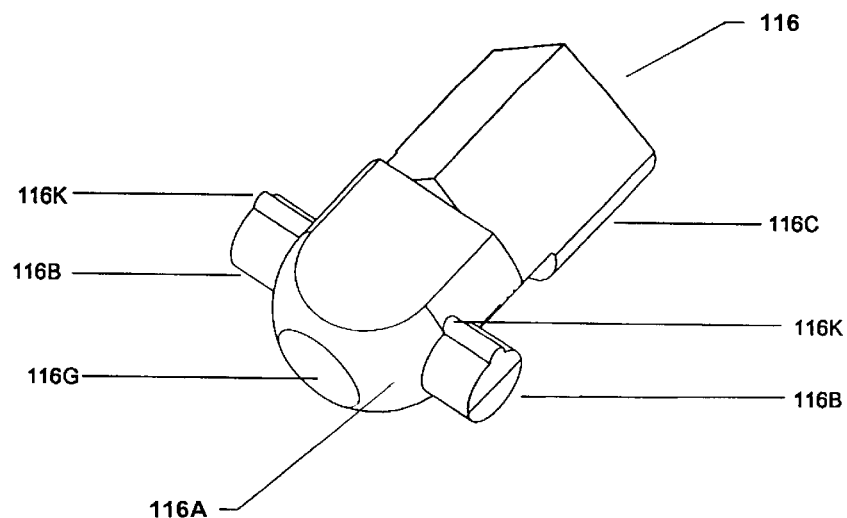
FIGS. 12A through 12G illustrate a pivoting or rotating joint for use with a second embodiment of Applicant's present invention.
Figure 12B:
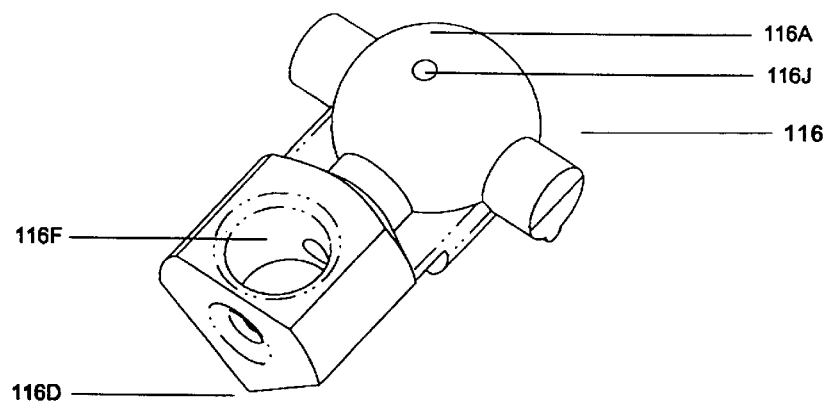
Figure 12C:
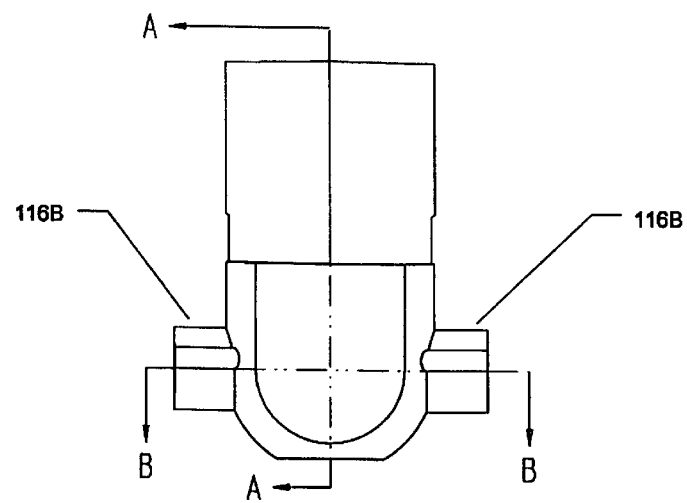
Figure 12D:
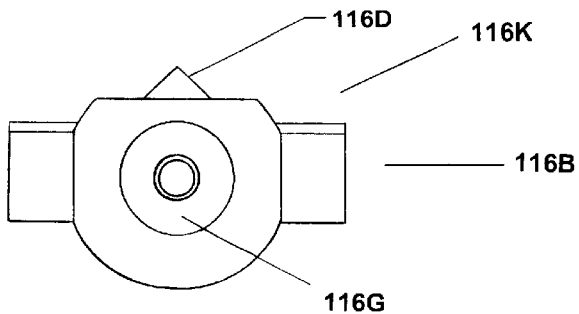
Figure 12E:
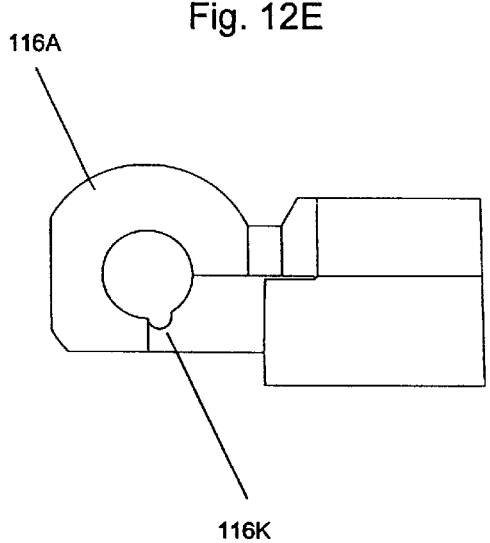
Figure 12F:
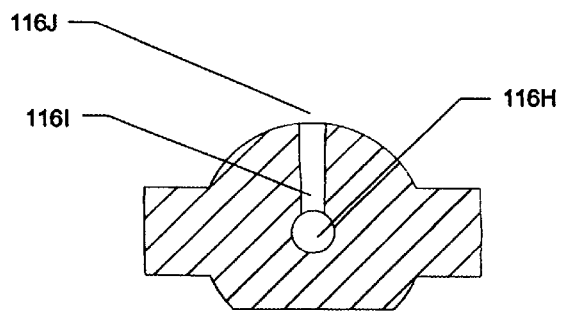
Figure 12G:
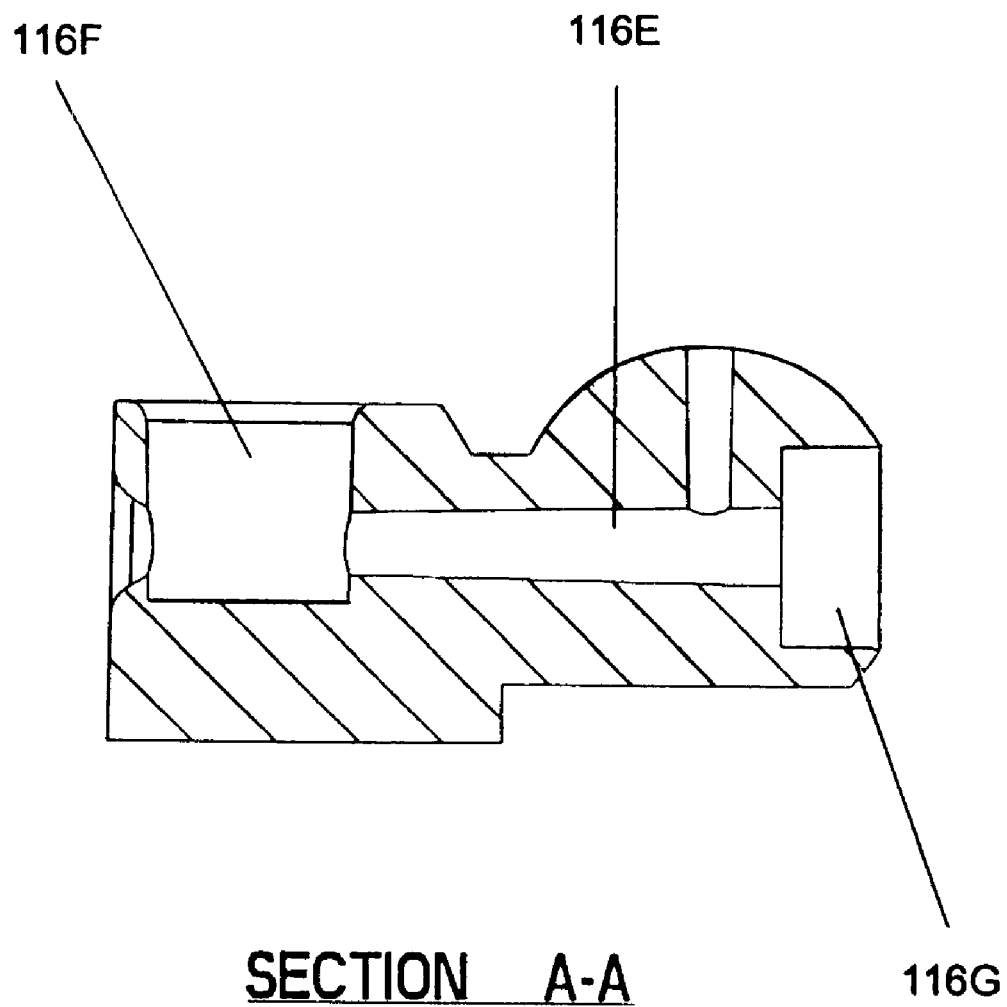

FIGS. 17A through 17F illustrate details of Applicants lock (117). Lock (117) is seen to include a nose portion (117A) with a fan shaped tail (117B). The lock includes a pair of tabs (117C) and (117D) on the underside thereof. The tabs project below the tail portion and are designed to engage channels (114O' and 114O") and the slot created by the left and right cover engaged to the base that is best illustrated in FIG. 10I. These tabs are then seen to lock in and attach the lock to the unit created by the combination of the base and the left and right cover. Note with preference to FIG. 10I that the lock cannot slide out due to the interference of the tabs with wall (122"Z) of left cover (122"). There is a corresponding wall (122'Z) on the right cover (122').

Lock (117) is also seen to have wings (117E) and (117F). Each wing having a boss (117G) and (117H) near a rearward end thereof. Wings (117E) and (117F) will, when the lock is slid forward to a closed or engaged position (as in FIGS. 10F, 10G, 10H, 10I, and 10J) will place the wings in slots (122'P) and (122"P) of right and left cover respectively. Further, it may be seen that bosses (117G and 117H) will snugly engage coves (122'R) and (122"R) of right and left cover respectively when the cover is pushed in to an engaged position where it lockingly engages the rotating joint. This coupling of the bosses and the coves will help secure the lock in a closed or engaged position. The lock prevents the rotating joint from rotating out of a down or use position (See FIG. 10H).

Figure 18A:
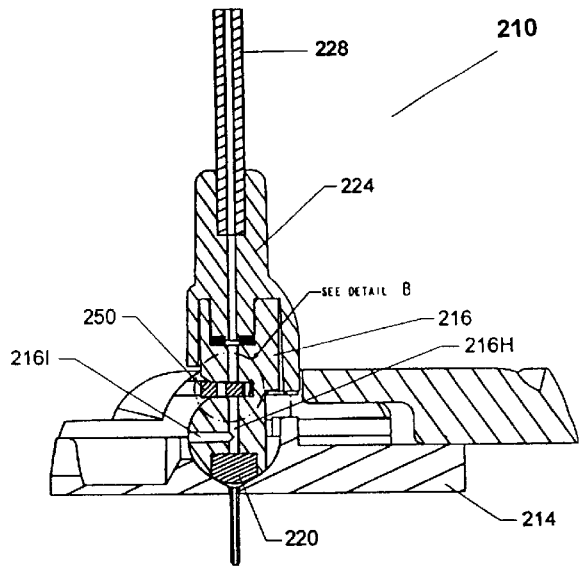
FIGS. 18A through 18F illustrate another embodiment of Applicant's present invention including a novel sliding hinge valve.
Figure 18B:
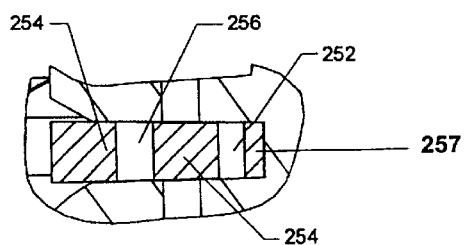
Figure 18C:
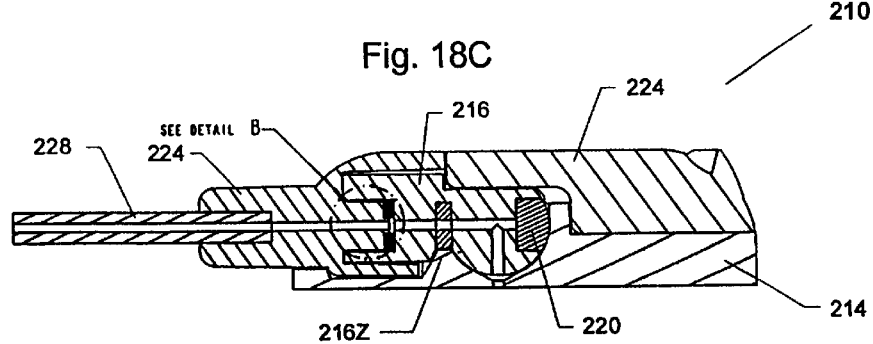
Figure 18D:
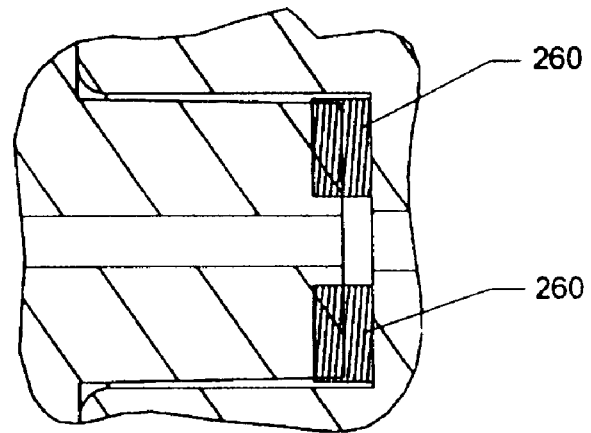
Figure 18E:
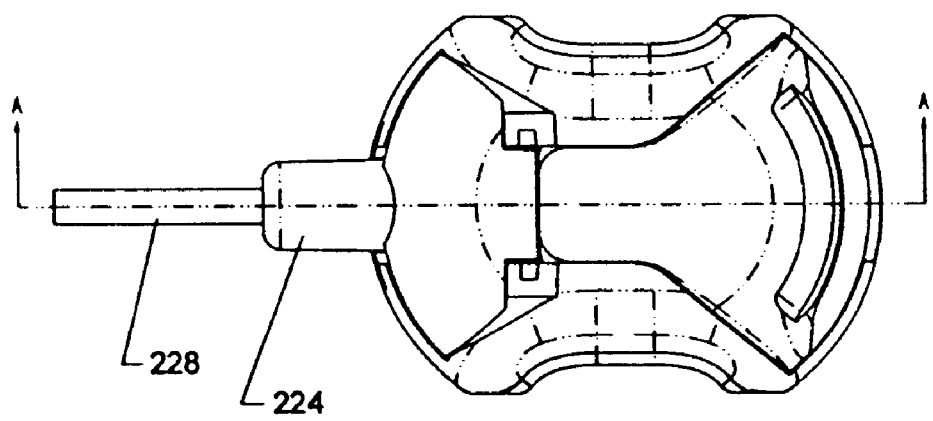
Figure 18F:
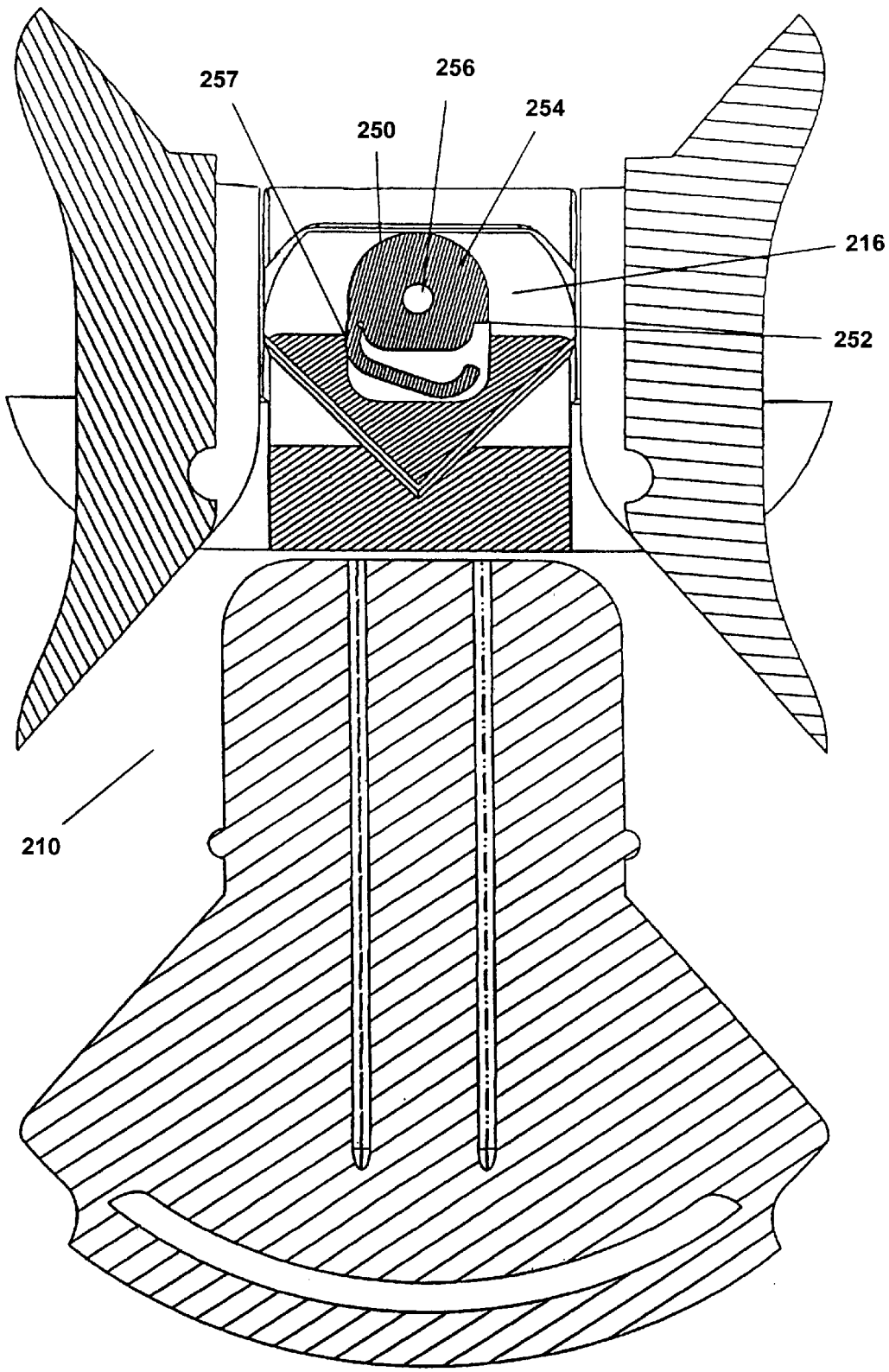

FIGS. 18A through 18F illustrate another alternate preferred embodiment of a fluid injection assembly (210) which includes a rotating joint (216) which contains a slide valve (250) which slides back and forth in a slide valve chamber (252). The slide valve (250) includes a valve body (254) which includes walls defining a channel (256). The valve body (254) is designed to snugly fit adjacent the walls defining slide valve chamber (252). Slide valve (250) may slide back and forth in slide valve chamber (252) on a "living" hinge (257). In an "out" position as illustrated in FIGS. 18A, 18B and 18F, the slide valve body urged by hinge (257) blocks the channel of central portion (216H) of central bore of joint (216). This is the position of the slide valve when fluid connector (224) is engaged therewith but rotating joint (216) in an "up" position, or, in fact, in any position but down. Note however, that when fluid connector (224) is rotated to a down position such as illustrated in FIG. 18C, then interference with walls (214Z) of base (214) causes slide valve (250) to move into a position such that channel (256) of slide valve (250) is aligned with central bore and liquid can pass through ball joint (216) and into the patient through the cannula (214C) extending downward from the base (214). The use of the slide valve makes the first septum of the previous embodiments unnecessary, and therefore a needle on fluid connector (224) is, likewise, unnecessary. Instead, the embodiments set forth in this set of drawings uses gaskets (260) where the channel of the fluid connector meets the rotating joint (see FIG. 18D). Gaskets (260) help provide a fluid tight fit with the fluid connector (224) to the ball joint (216) when the ball joint and fluid connector are engaged.

Figure 19A:
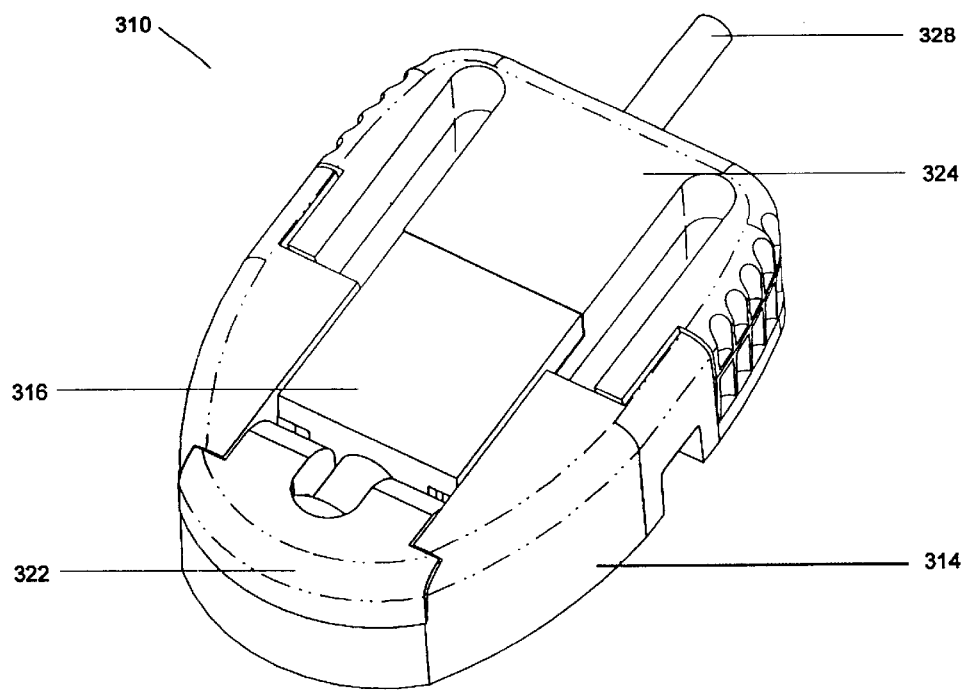
FIGS. 19A through 19E illustrate various views of yet another embodiment of Applicant's present invention.
Figure 19B:
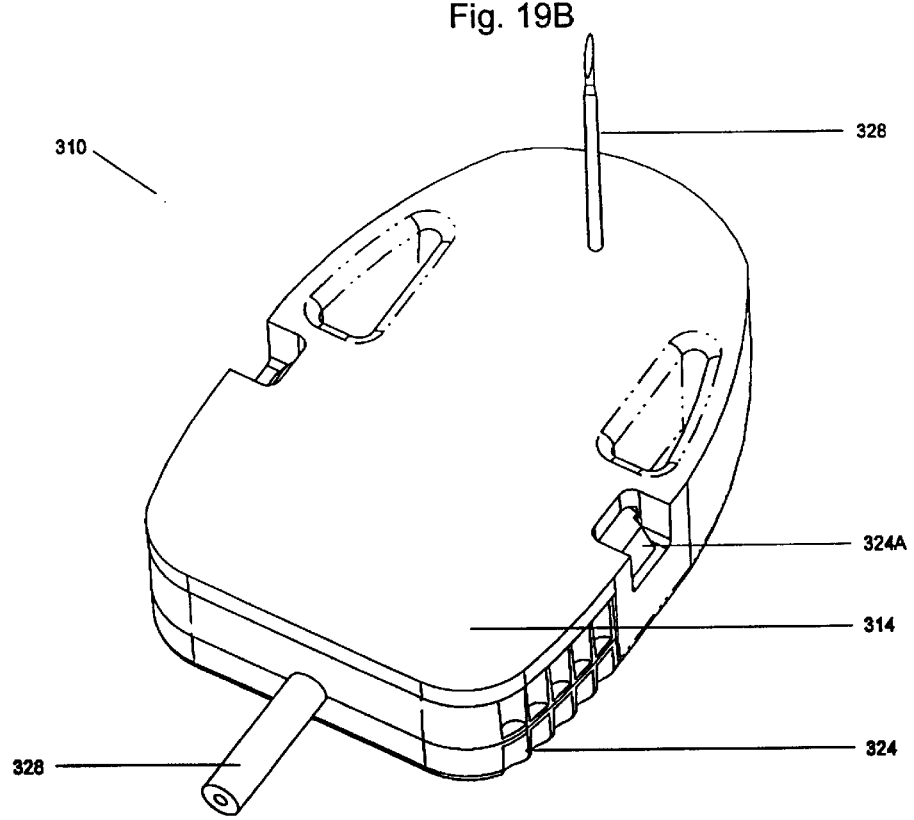
Figure 19C:
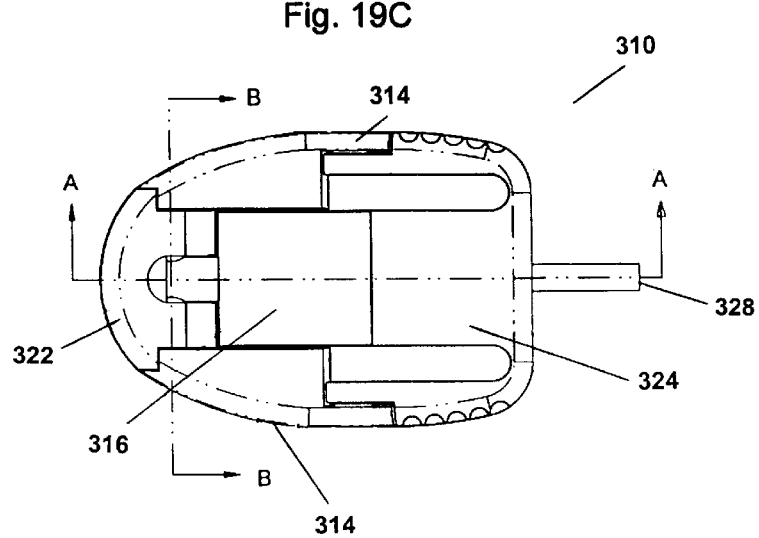
Figure 19D:
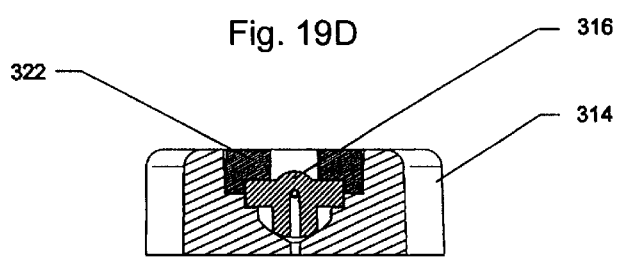
Figure 19E:
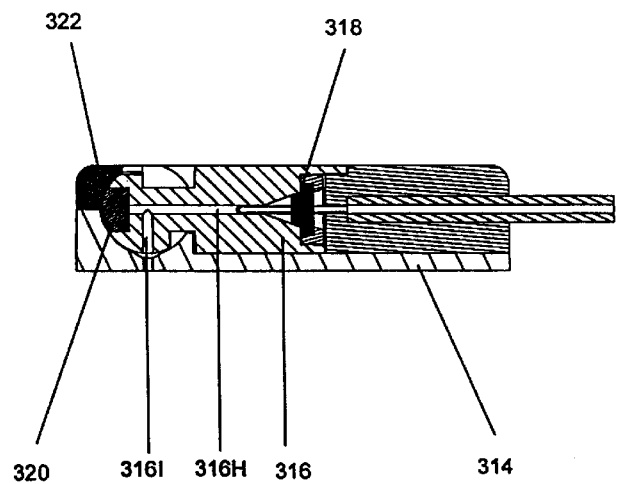
Figure 19F:
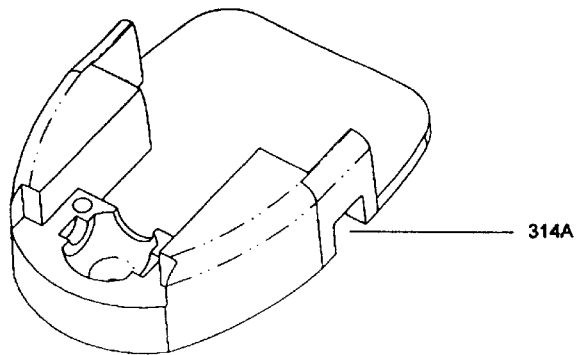
FIGS. 19F through 19N illustrate various views of the various component parts of the embodiment of Applicant's present invention that is illustrated in FIGS. 19A through 19E.
Figure 19G:
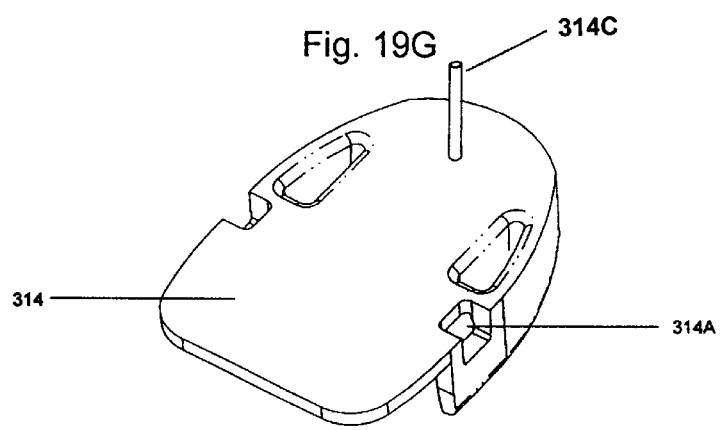
Figure 19H:
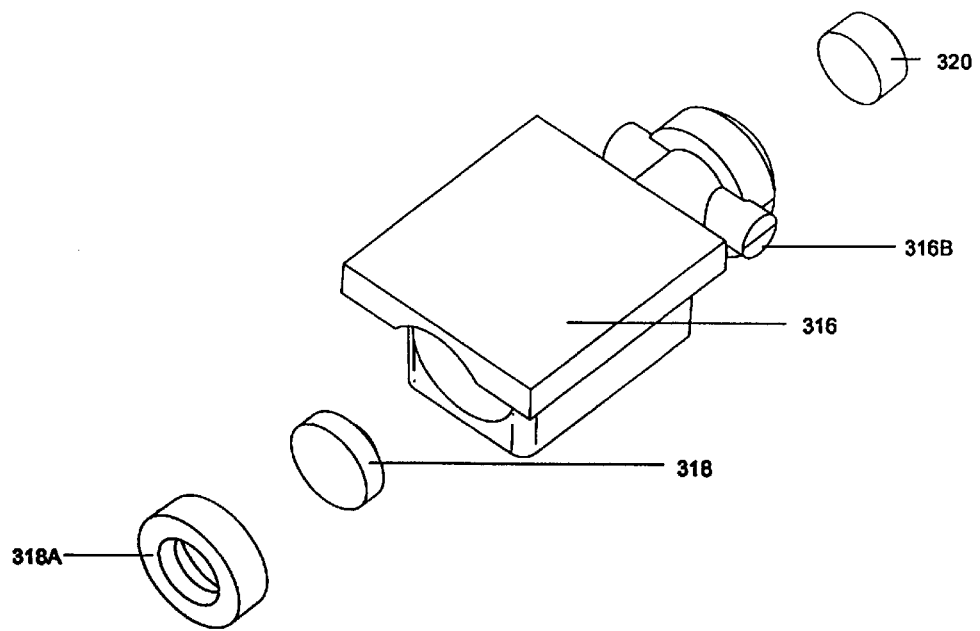
Figure 19I:
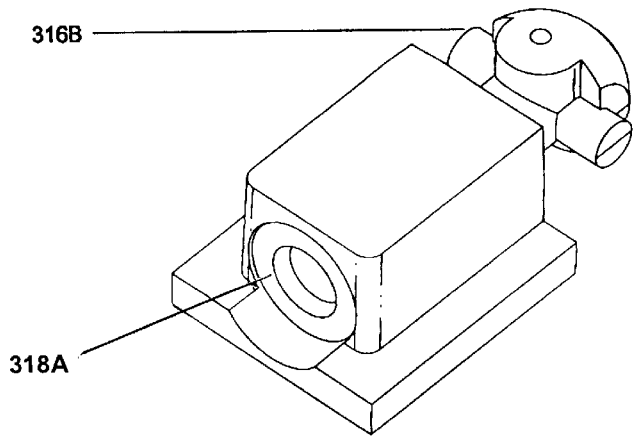
Figure 19J:
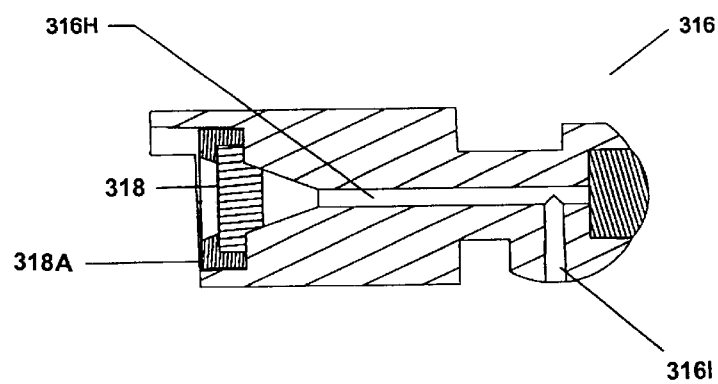
Figure 19K:
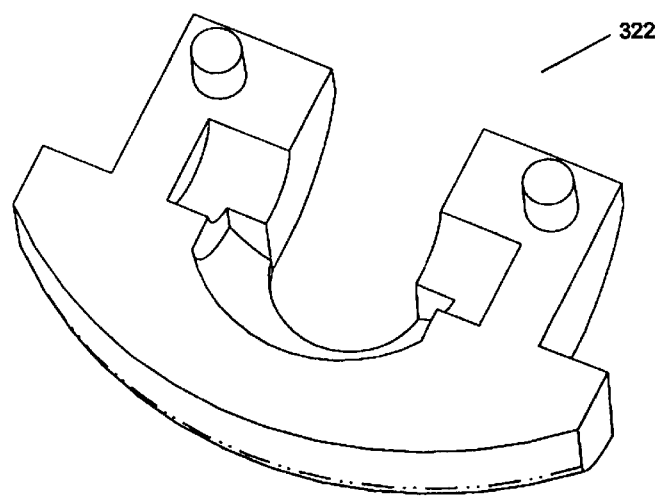
Figure 19L:
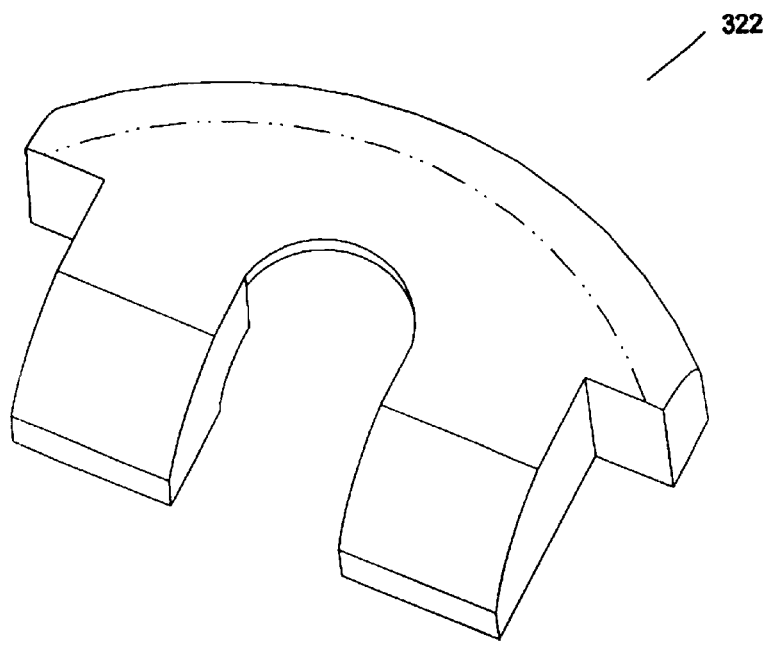
Figure 19M:
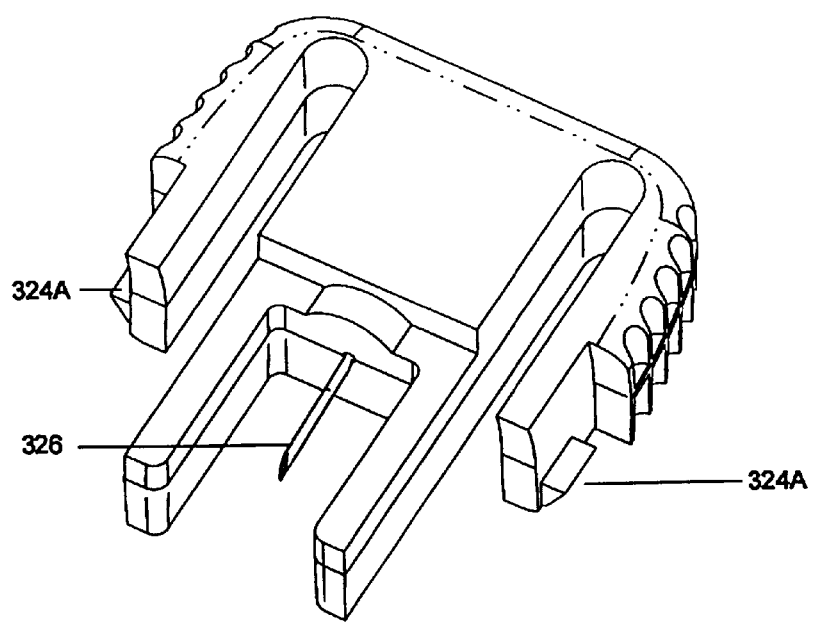
Figure 19N:
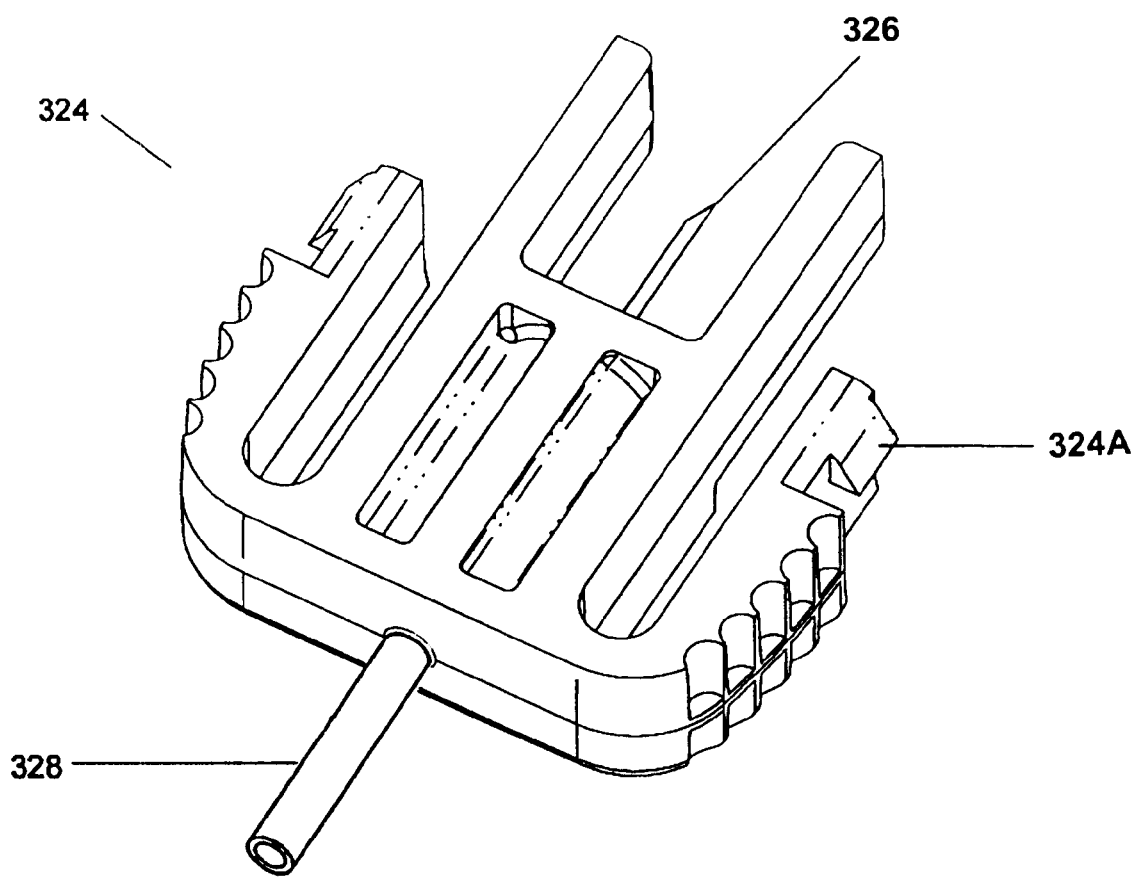

Yet another embodiment of Applicant's fluid injection assembly (310) featuring the unique pivoting joint concept is illustrated in FIG. 19A through 19N. With the details of the earlier embodiments understood, this embodiment is seen to provide a one piece base (314) at least partially cut out to receive part of a pivoting joint (316) (see FIGS. 19E and 19F). Pivoting joint (316) lays in base (314) and is partially engaged with a one piece cover (322) for engaging support arms (316B). Note in FIGS. 19M and 19N that connector (324) includes arms (324A) that will engage slots (314A) of base (314) (See FIGS. 19F and 19G) and also includes needle (326) and feed tube (328). As seen in FIG. 19E, pivoting joint (316) is seen to have a first septum (318) and second septum (320). The first septum is held in place in the rotating joint by means of a cap (318A) (See FIGS. 19H and 19I). In FIG. 19J the two channels or bores (316H) and (316I) within the rotating joint may be seen, the bores are functionally equivalent to those seen in earlier rotating joints. In FIGS. 19K and L cover (322) can be seen with cutouts for at least partially enclosing the pivoting joint and legs for engaging the base.

Figure 20A:
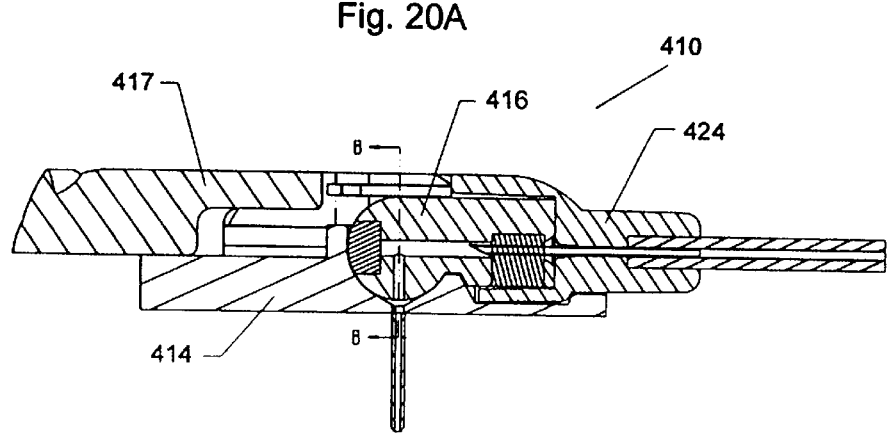
FIGS. 20A through 20C illustrate yet another alternate preferred embodiment of Applicant's present invention including a novel pivoting joint.
Figure 20B:
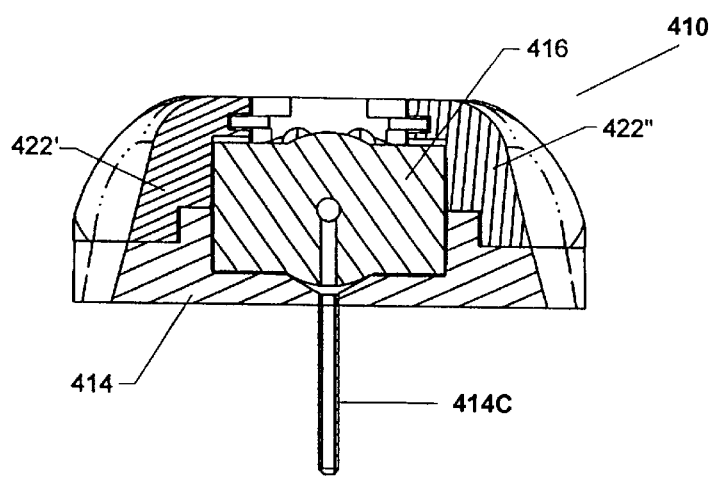
Figure 20C:
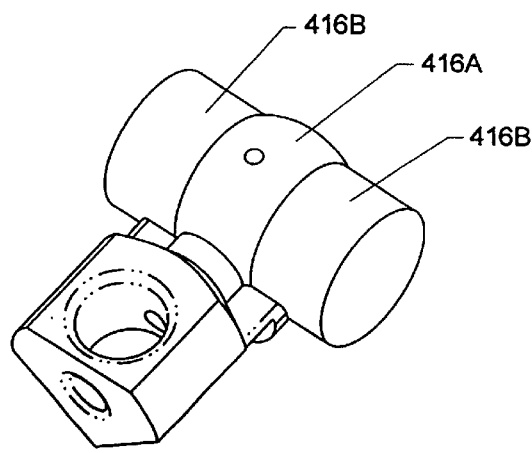

FIGS. 20A through 20C illustrate yet another alternative preferred embodiment of applicants unique fluid injection assembly (410) having a "T" shaped rotating joint (416). Here it is seen that alternate preferred embodiment of fluid injection assembly (410) has a base (414) and a pair of covers (422') and (422") which together will enclose a cylindrical portion (416A) and cylindrical support legs (416B) of the "T" joint in a manner that will allow the "T" joint (416) to pivot from a down position where fluid can be carried through fluid connector (424) into "T" joint (416) and down through cannula (414C) into the patient. In an up or vertical position (not shown) a handle may engage the unit to insert the fluid injection assembly onto the patient. This alternate preferred embodiment also features a lock mechanism (417).

This alternate preferred embodiment is provided to, among other things, illustrate the diverse configurations that may be obtained with Applicant's unique pivoting joint. Each of the designs have a joint that pivots with respect to the body and/or covers of the fluid injection assembly allowing an insertion of a needle, the needle carried on the handle for placing the fluid injection on the patient. However, the pivoting or rotating joint, whether it be "T" shaped, ball shaped or any other shape, provides, in a down position, fluid communication between a connector and a cannula for providing fluid infusion to the patient.

The main assembly and the rotating joint may be made from antibacterial material known in the art.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A system for the subcutaneous delivery into the body of a patient, of a fluid, from a remote vessel, the system comprising:

main assembly emplacement member having a needle thereon;

a delivery tube having a near end and a removed end, the delivery tube for carrying a fluid, the delivery tube attached at the near end to the remote vessel and at the removed end having a rotating member engagement device, which includes a needle; and a main assembly including a body having a cannula depending therefrom and a rotating member, including an engagement arm of the rotating member for rotating with respect to the body, from a first position providing axial alignment of the engagement arm of the rotating member with the cannula to a second position, the second position providing fluid communication between a removed end of the engagement arm of the rotating member and the cannula when the delivery tube is attached thereto.

2. The system of claim 1 wherein the rotating member is a ball joint and the engagement arm includes a first septum.

3. The system of claim 2 wherein the ball joint includes a second septum positioned such that when the ball joint is in the first position, the first and second septum are aligned with the cannula.

4. The system of claim 3 wherein the engagement arm is elongated and includes a channel and the first septum is located at one end of the channel and a second end of the channel is in communication with the cannula when the rotating member is in the second position.

5. The system of claim 4 wherein a third end of the channel is in communication with the second septum.

6. The system of claim 2 wherein the ball joint includes support arms projecting therefrom for rotatably supporting the ball joint with respect to the body of the main assembly.

7. The system of claim 1 wherein the body of the main assembly includes means to releaseably retain the engagement arm of the rotating member in the second position when the rotating member engagement device is attached thereto.

8. The system of claim 1 wherein the body of the main assembly includes audible means to releasably retain the engagement arm of the rotating member in the second position when the rotating member engagement device is attached thereto.

9. The system of claim 1 wherein the engagement arm of the rotating member projects above the upper surface of the body when in the first position, but does not project above the surface of the body when in the second position.

10. The system of claim 1 wherein the rotating member engagement device of the delivery tube includes a guide for aligning it with the engagement arm of the rotating member.

11. The system of claim 1 further including a plug, engageable with the engagement arm of the rotating member, the plug for engagement with the engagement arm of the rotating member when the delivery tube is not engaged therewith.

12. The system of claim 1 wherein the main assembly is made from an antibacterial material.

13. In a system for the subcutaneous delivery of a fluid to a patient, the system including a remote fluid source and a delivery tube connected at a first end to the remote fluid source and having a needle at a second end thereof, the system having a body with a cannula engaged therewith, the cannula for placement into the patient's skin, an improvement, the improvement comprising: a rotatable joint for engagement with the body of the system, the joint including a joint body and a first engagement arm, the engagement arm having a first septum, the joint body having walls defining a channel therein, the channel aligned in fluid communication with the cannula when the rotatable ball joint is in a second position and away from the cannula when the rotatable joint in a first position.

14. The improvement of claim 13 wherein the rotatable joint includes a second septum engaged with the channel walls such that the second septum is aligned with the first septum and the cannula when the rotatable ball joint is in the first position.

15. The improvement of claim 14 wherein the channel of the rotatable joint provides fluid communication between the first septum and the second septum.

16. The improvement of claim 15 wherein the rotatable joint is dimensioned for receipt into the body such that rotation to the second position places the first septum and the second septum and at least part of the channel in axial alignment with the cannula.

17. The improvement of claim 13 wherein the rotating joint is made of an antibacterial material.

18. The improvement of claim 13 wherein the rotating joint includes means to releaseably retain the joint to the body in the first position and also to releaseably retain the joint to the body when the joint is in the second position.

19. The improvement of claim 13 wherein the body of the joint includes means to slidably receive the second end of the delivery tube so as to guide the needle of the delivery tube into the first septum.

20. The improvement of claim 13 wherein at least part of the channel is perpendicular to the cannula and at least part of the channel is parallel to the cannula when the rotatable joint is in the first position.

21. The improvement of claim 13 wherein the first septum is recessed into the first engagement arm of the rotatable joint, the second septum is flush with the surface of the joint body.

22. The improvement of claim 13 further including a handle having a needle, and wherein at least part of the channel is dimensioned for receipt of the needle therein.

* * * * *